United States Patent [19]

Meanwell

[11] Patent Number: 4,994,482
[45] Date of Patent: Feb. 19, 1991

[54] ARYLPYRAZOL DERIVATIVES AS ANTI-PLATELET AGENTS, COMPOSITIONS AND USE

[75] Inventor: Nicholas A. Meanwell, East Hampton, Conn.

[73] Assignee: Bristol-Myers Squibb Company, New York, N.Y.

[21] Appl. No.: 523,637

[22] Filed: May 10, 1990

Related U.S. Application Data

[63] Continuation-in-part of Ser. No. 387,749, Jul. 31, 1989, abandoned.

[51] Int. Cl.⁵ .................. A61K 31/415; C07D 231/12
[52] U.S. Cl. ..................................... 514/406; 548/378
[58] Field of Search ........................ 548/378; 514/406

[56] References Cited

U.S. PATENT DOCUMENTS 4,072,498  2/1978  Moon et al. ......................... 548/378
4,916,150  4/1990  Bailey et al. ......................... 548/378

Primary Examiner—Robert W. Ramsuer
Attorney, Agent, or Firm—Aldo A. Algieri

[57] ABSTRACT

Compounds of the formula

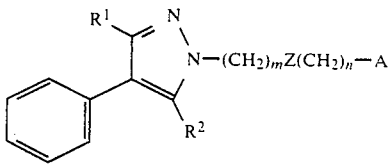

wherein
$R^1$ and $R^2$ each are independently hydrogen or phenyl, provided that $R^1$ and $R^2$ may not both be hydrogen;
m is an integer from 3 to 9;
n is an integer from 0 to 3 and the sum of m+n is an integer from 5 to 12;
Z is O, S, SO, $SO_2$, —CH=CH— or a direct bond;
A is

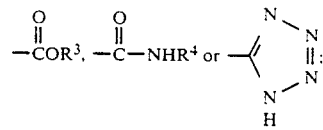

$R^3$ is hydrogen or $C_{1-6}$ alkyl; and
$R^4$ is hydrogen, $C_{1-4}$ alkyl or methylsulfonyl;
and pharmaceutically acceptable salts or hydrates thereof are novel inhibitors of adenosine diphosphate and collagen-induced aggregation of human platelet-rich plasma and are particularly useful as inhibitors of mammalian blood platelet aggregation.

17 Claims, No Drawings

ARYLPYRAZOL DERIVATIVES AS ANTI-PLATELET AGENTS, COMPOSITIONS AND USE

CROSS-REFERENCE TO RELATED APPLICATION

This application is a continuation-in-part of copending application Ser. No. 387,749, filed July 31, 1989 now abandoned.

BACKGROUND OF THE INVENTION

This invention relates to novel pyrazole compounds having valuable pharmacological properties and to their preparation and use. In particular, the invention is concerned with a series of new IH-substituted arylpyrazole derivatives which are inhibitors of blood platelet aggregation.

Various derivatives of tetrahydroimidazo[2,1-b]quinazolin-2-one and 2,3-dihydro-2-oxo-imidazo[4,5-b]quinolin-2-one have been described and shown to be useful as blood platelet antiaggregative and cardiotonic agents. Representative examples of these two classes are:

Chodnekar et al., U.S. Pat. No. 4,256,748, issued on Mar. 17, 1981, describes a series of compounds having the formula

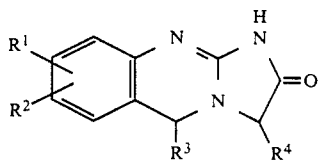

Representative of the Chodnekar compounds are RO 15-2041 $R^4=CH_3$, $R^3=H$, $R^2=6-CH_3$, $R^1=7-Br$) and RO 13—6438 ($R^4=CH_3, R^3=H$, $R^2=6-CH_3$, $R^1=H$).

Meanwell et al., U.S. Pat. No. 4,668,686, issued on May 26, 1987, describes a series of compounds having the formula

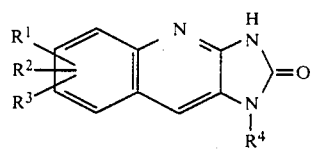

Representative of the Meanwell compounds is BMY-20844 wherein $R^1=H$, $R^2=7-CH_3$, $R^3=8-CH_3$ and $R^4=H$.

A different class of compounds from those described above are a series of substituted imidazol-2-yl alkanoic acid derivatives which are reported to be useful as anti-thrombotic, anti-inflammatory, antiatherosclerotic and lipid lowering agents.

Lautenschlager et al., in U.S. Pat. No. 4,460,598 issued July 17, 1984 describes a series of triphenylimidazol-2-yloxyalkanoic acids having the formula

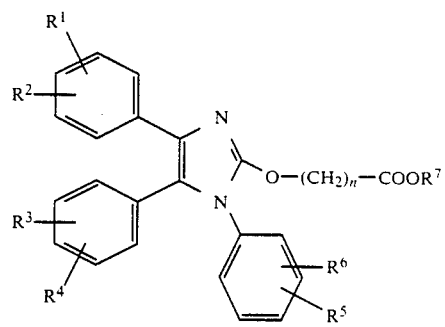

wherein $R^1$, $R^2$, $R^3$, $R^4$, $R^5$ and $R^6$ each are H, halogen, alkyl, alkoxy and trifluoromethyl; n is an integer of 1 to 10 and $R^7$ is H, alkali metal ions, alkyl or benzyl group. A particularly preferred member of the series wherein $R^1$ to $R^6$ is hydrogen, n is 7 and $R^7$ is sodium, is identified in the art as octimibate sodium and has been studied extensively, for example, Lautenschlager et al., Drugs of the Future, 1986; 11(1), 26; Ibid, 1987; 12, 84; Ibid, 1988; 13(1), 81. Although octimibate is described as possessing anti-aggregatory activity, it is being developed in man as an antihyperlipidemic agent.

German Patent applications Nos. DE-3,504,677, 3,504,678, 3,504,679 and 3,504,680 all published on Aug. 14, 1986, and European Patent Application No. EP-130,526, published on Sept. 1, 1985, describe a large number of substituted imidazol-2-yl derivatives similar to the above-mentioned U.S. Pat. No. 4,460,598.

European Patent Application No. EP-248,594, published on Dec. 9, 1987, describes a series of 1,5-Diphenyl-3-substituted pyrazole compounds of formula

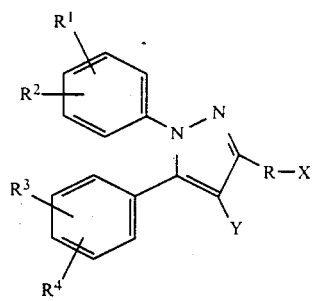

wherein Y is H, Br, Cl, or lower alkyl: R is $C_{2-16}$ optionally unsaturated straight chain hydrocarbon group and $R^1$, $R^2$, $R^3$, $R^4$ and X represent various substituents. These compounds are reported to inhibit cyclooxygenase and/or lipoxygenase pathway(s) and are useful for alleviating inflammation, asthma, hypersensitivity, myocardial ischaemia, dermatological conditions and gastrointestinal inflammatory conditions.

SUMMARY OF THE INVENTION

In its broadest aspect, this invention relates to a new series of IH-substituted arylpyrazole derivatives having the formula

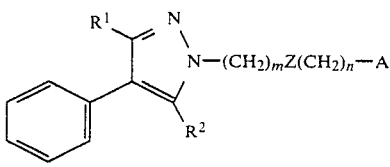

wherein $R^1$, $R^2$, m, Z, n and A are as defined below, and their pharmaceutically acceptable salts and hydrates which are potent inhibitors of adenosine diphosphate and collagen-induced aggregation of human platelet-rich plasma and are particularly useful as inhibitors of mammalian blood platelet aggregation.

Another embodiment of the invention relates to pharmaceutically acceptable compositions comprised of a compound of Formula I combined with at least one pharmaceutically acceptable excipient. Further embodiments of this invention relate to a method for inhibiting blood platelet aggregation and a method for treating hyperlipoproteinemia in a mammal which comprises administering a therapeutically effective amount of a compound of Formula I or a pharmaceutically acceptable salt or hydrate thereof to a mammal in need of such treatment.

DETAILED DESCRIPTION OF THE INVENTION

This invention relates to inhibitors of mammalian blood platelet aggregation of the formula

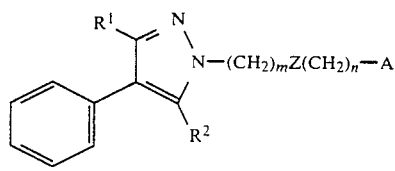

wherein
$R^1$ and $R^2$ each are independently hydrogen or phenyl, provided that $R^1$ and $R^2$ may not both be hydrogen;
m is an integer from 3 to 9;
n is an integer from 0 to 3 and the sum of m+n is an integer from 5 to 12;
Z is O, S, SO, $SO_2$, —CH=CH— or a direct bond;
A is

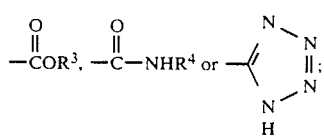

$R^3$ is hydrogen or $C_{1-6}$ alkyl; and
$R^4$ is hydrogen, $C_{1-4}$ alkyl or methylsulfonyl;
or a pharmaceutically acceptable salt or hydrate thereof.

As used herein, the terms "$C_{1-4}$ alkyl and $C_{1-6}$ alkyl" refer to branched and unbranched saturated hydrocarbon chain; for example, methyl, ethyl, n-propyl, isopropyl, n-butyl, tert-butyl, n-pentyl, n-hexyl and the like. The term "pharmaceutically acceptable salts" means the salt of a compound of Formula I with a nontoxic pharmaceutically acceptable organic or inorganic base. Such bases are well known and include sodium, potassium, lithium, calcium magnesium and tetramethylammonium. We have also found that many of the compounds of Formula I produced herein tenaciously hold water. In some cases it appears that the products are true hydrates and hemi-hydrates, while in other cases the products may merely retain adventitious water of hydration. The Examples below give the amount of water (where appropriate) and the analyses and melting points are those of the hydrated product unless otherwise specified.

In the compounds of Formula I, $R^1$ and $R^2$ are preferably hydrogen or phenyl, and more preferably are phenyl. Preferably Z is a direct bond, —CH=CH—, oxygen or sulfur and, more preferably, Z is a direct bond or oxygen. It is preferred that m is 3 to 9, n is 1 to 3 and that the sum of m+n is 6 to 10. When Z is a direct bond, m+n is preferably 7 to 10 and when Z is —CH=CH—, m is preferably 3 or 5 and n is 3. Preferably m is 5 or 6 and n is 1 when Z is oxygen or sulfur and preferably m is 6. Substituent A is preferably

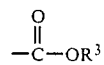

or tetrazolyl and preferably A is carboxy.

The compounds of Formula I may be prepared by various procedures, preferably starting from the known compounds of Formula IIb or XXVIII.

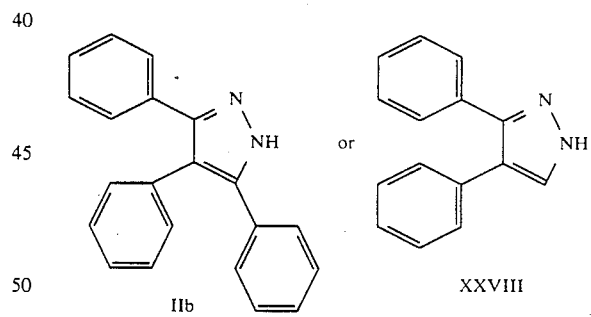

The various synthetic and alternate procedures used for the preparation of compounds of Formula I will depend on the desired compound to be produced and the particular values of m, n, Z and A. For example, when Z is a direct bond, the general procedures outlined in Schemes 1, 2 and 3 may be used to prepare compounds of Formula I.

The compounds of Formula I wherein $R^1$ and $R^2$ are phenyl, Z is a direct bond, n is zero and A is

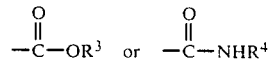

may be prepared by the procedure as shown in Reaction Scheme 1.

Reaction Scheme 1

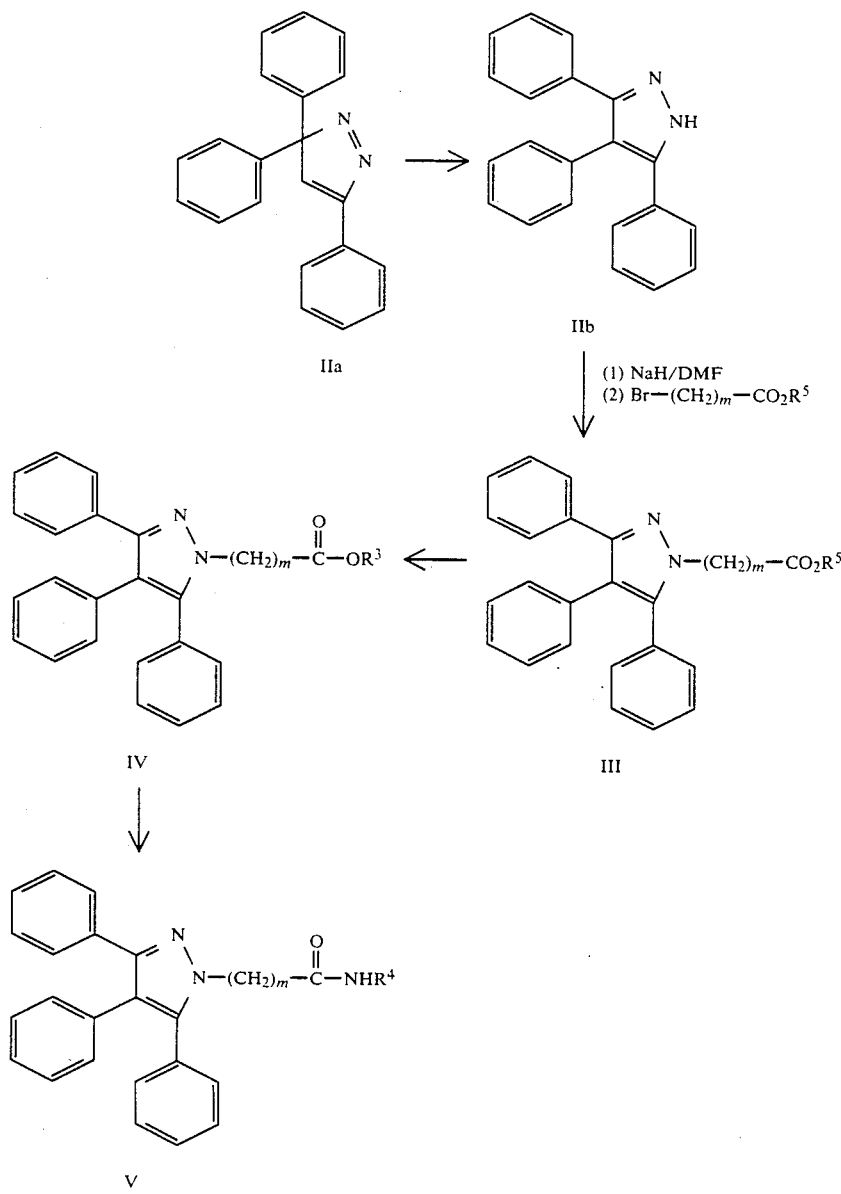

The preparation of 3,4,5-triphenyl-1H pyrazole of Formula IIb was generally done as described by W. Kimse and L. Homer, *Annalen,* 1958, 614, 1, via a cycloaddition reaction of diphenyldiazomethane to phenylacetylene to produce the cycloadduct of Formula IIa which is reported to rearrange at room temperature to produce the compound of Formula IIb. The starting diphenyldiazomethane was itself prepared by oxidation of benzophenone hydrazone using the procedure described by L. I. Smith and K. L. Howard in *Organic Syntheses,* 1955, Coll. Vol. III, 351 and modified by the procedure of J. B. Miller, *J. Org. Chem.,* 1959, 24, 560. However, the product isolated by the above procedure proved to be the cycloadduct of Formula IIa with no trace of the pyrazole of Formula IIb as ascertained by thin layer chromatography (TLC) analysis. It was subsequently found that upon heating at 100° C. for 30 minutes the pyrazole of Formula IIa rearranged to the pyrazole of Formula IIb. Alternatively, it was also found that heating a solution of the pyrazole of Formula IIa in dimethylformamide (DMF) on a steam bath in the presence of a slight excess of sodium hydride effected rearrangement to the pyrazole of Formula IIb and also resulted in salt formation to provide a solution of anion of the Formula IIb.

The compounds of Formula I may be prepared by various procedures. In one procedure which is illustrated in Reaction Scheme 1, an anion solution of the intermediate of Formula IIb is alkylated at about room temperature in a inert organic solvent with an ester of an ω-bromoalkanoic acid to produce the pyrazoles of Formula III. The esters of Formula III may then be hydrolyzed by standard procedures such as basic hydrolysis to produce the corresponding pyrazole carboxylic acids of Formula IV wherein $R^3$ is hydrogen. The carboxylic acid may, if desired, be converted to a pharmaceutically acceptable salt by methods well known in the art. In addition, the carboxylic acids of Formula IV may be converted to amides of Formula V by first converting the acid to a chemically reactive species such as an acid chloride by using standard chlorinating agents such as oxalyl chloride, phosphoryl chloride and the like.

Alternatively, as in the instance wherein $R^4$ is methylsulfonyl, it is preferred to activate the carboxylic acid with 1,1-carbonyldiimidazole in an inert organic solvent such as tetrahydrofuran at a temperature of about room temperature to reflux temperature and then treating with methanesulfonamide followed by the addition of a base such as 1,8-diazabicyclo[5.4.0]undec-7-ene.

The esters of ω-bromoalkanoic acid are either commercially-available such as ethyl 6-bromohexanoate and ethyl 4-bromobutyrate or available as an acid such as 8-bromoctanoic acid which is esterified with methanol or ethanol in the presence of sulfuric acid. Alternatively, as in the case with methyl 9-bromononanoate which is described by G. C. Barley et al. in *J. Chem. Soc.* (C), 1973, 151, it may be synthesized from commercially-available, azelaic acid monomethyl ester by way of selective reduction of the carboxylic acid with borane-tetrahydrofuran or borane dimethylsulfide similar to the procedures described by N. M. Yoon et al. in *J. Org. Chem.*, 1973, 38, 2786 and followed by bromination with triphenylphosphine/bromine in dimethylformamide at about room temperature as described by D. R. Hepburn and H. R. Hudson in *J. Chem. Soc. Perkin I*, 1976, 754.

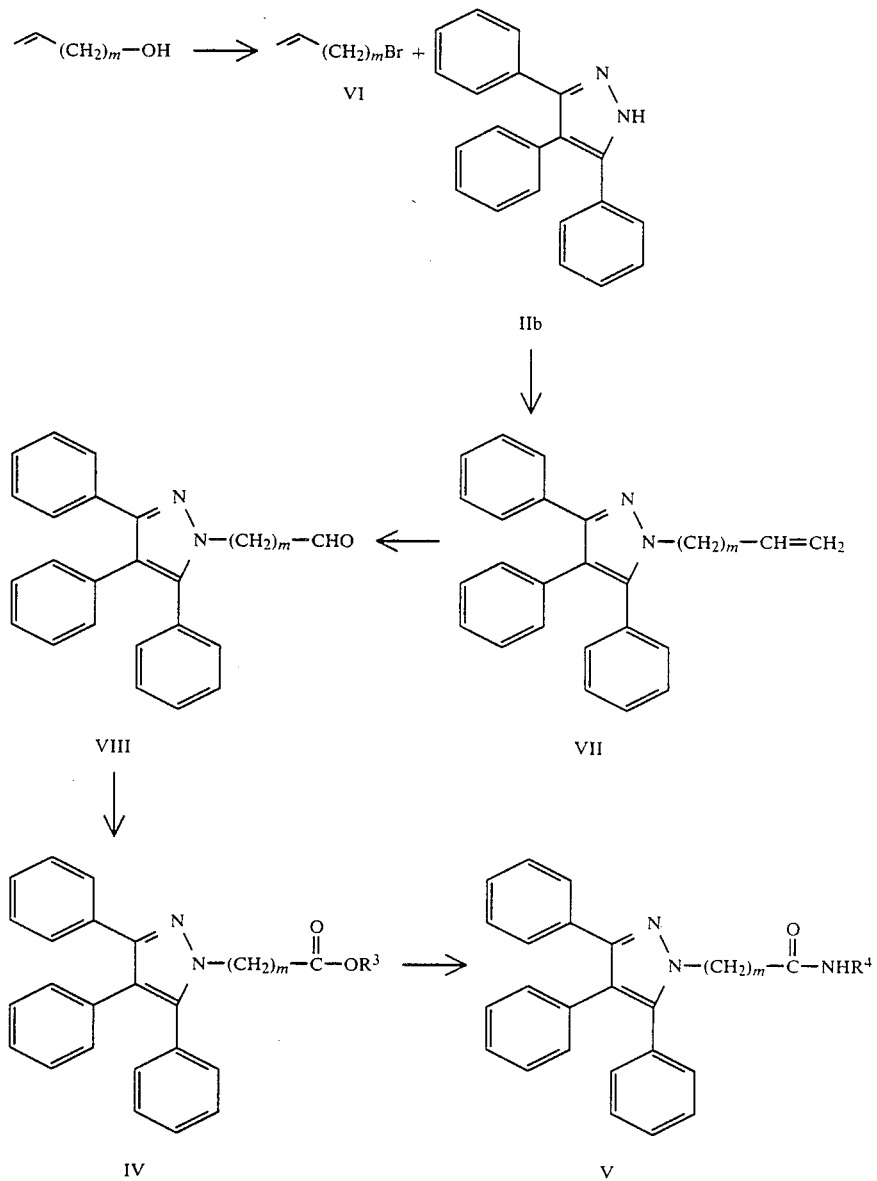

Reaction Scheme 2

In another procedure which is illustrated in Reaction Scheme 2, the sodium salt of the pyrazole of Formula IIb is alkylated with the bromoalkene of Formula VI which is itself prepared from the corresponding alcohol by bromination in an organic solvent and preferably dimethylformamide to produce the pyrazole intermediates of Formula VII. The vinyl moiety of Formula VII is subjected to ozonolytic degradation by standard procedures using ozone in an organic solvent at low temperatures to produce the aldehyde of Formula VII. The carboxylic acid of Formula IV is then prepared by oxidation of the aldehyde moiety of Formula VIII by methods well known in the art such as Jones reagent. The resulting acid may be converted to an ester, for example, methyl ester with methanol in the presence of an acid such as sulfuric acid or the acid of Formula IV may be converted to the amides of Formula V as described above in Reaction Scheme 1.

In still another procedure, the compounds of Formula I having either an extended saturated side chain or an unsaturated moiety in the side chain as when Z is —CH=CH— may be prepared from compounds of Formula III as depicted in Reaction Scheme 3.

Reduction of the ester of Formula III may be carried out by known procedures, for example, lithium aluminumhydride in an inert organic solvent such as diethyl ether and tetrahydrofuran to produce the alcohol of Formula IX which may then be oxidized to the aldehyde of Formula VIII by methods well-known in the art such as the use of pyridinium chlorochromate in dichloromethane. The incorporation of a vinylene moiety in the compound of Formula X may be carried out by the well-known Wittig reaction utilizing either commercially or readily available Wittig reagents, for example, 4-carboxybutyl triphenylphosphonium bromide in an inert organic solvent such as tetrahydrofuran in the presence of a base to produce the unsaturated acid of Formula X. Generally, a mixture of geometric isomers, (Z)cis and (E)trans. are produced in the Wittig reaction. However, the conditions of the reaction may be modified so as to produce predominantly one isomer as in the instant example wherein the ratio is about 3 to 1 of (Z) to (E) isomer. If desired, the cis and trans isomers may be separated by standard and well-known separation techniques such as column chromatography and variations thereof. The compounds of Formula X may then be readily converted to the compound of Formula XI as discussed above.

In addition to the procedures illustrated in Reaction Schemes 1 and 2, an extended saturated side chain for compounds of Formula I may be prepared by catalytic hydrogenation of the unsaturated moiety in cis. trans or mixtures of geometric isomers of the compounds of Formula X or XI. The hydrogenation reaction to produce compounds of Formula XII and XIII may conveniently be carried with hydrogen over 10% palladium on carbon at or slightly above atmospheric pressure in non-reducible organic solvents.

Reaction Scheme 3

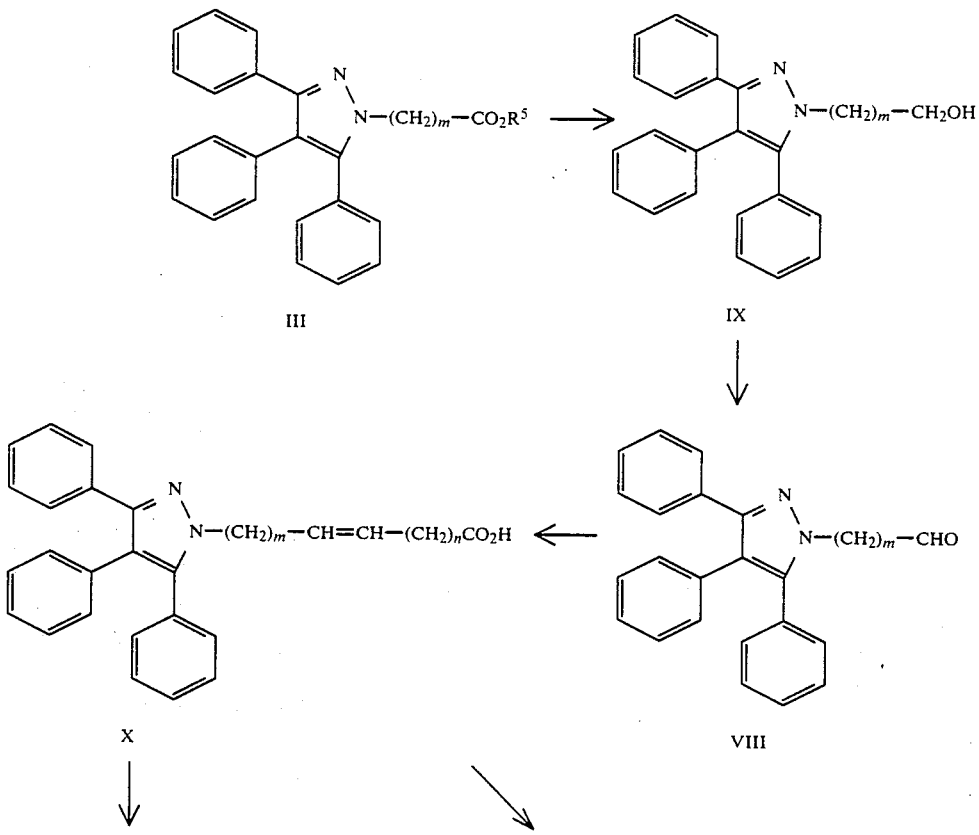

-continued
Reaction Scheme 3

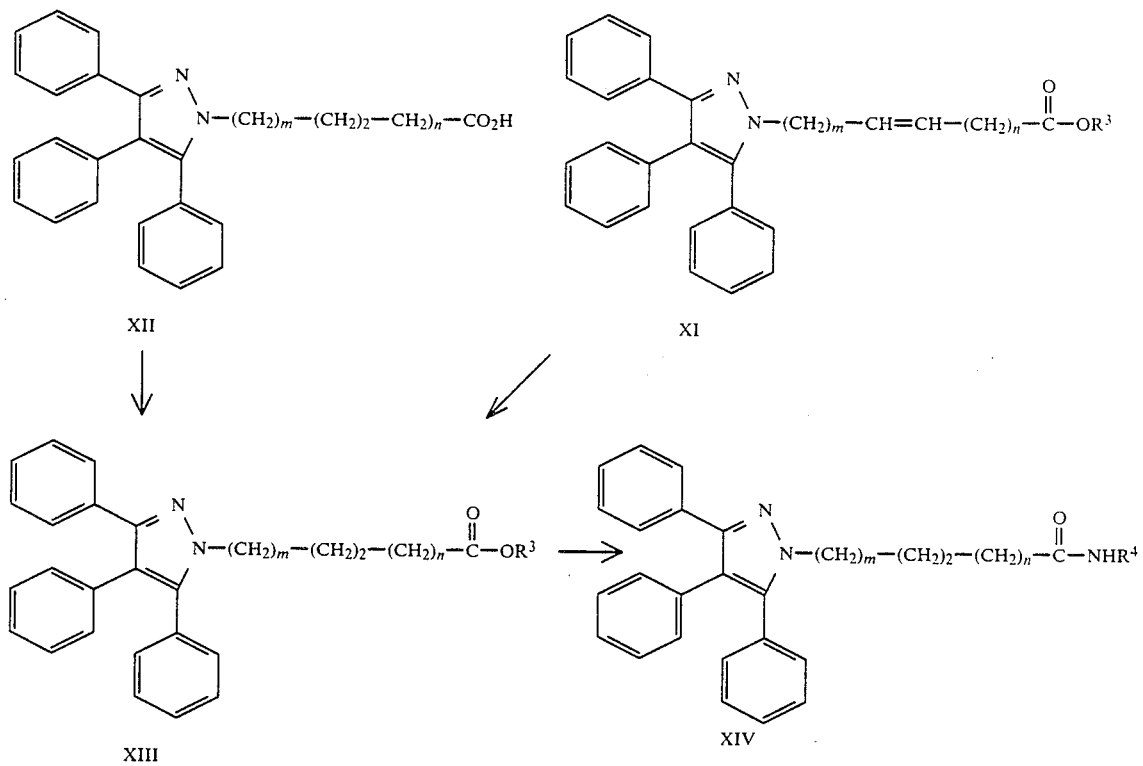

Substitution of the carboxylic acid moiety in the compounds of Formula I by an acidic tetrazole moiety may readily be carried out by the sequence of reactions illustrated in Reaction Scheme 4. Thus, the alcohol of Formula IX is converted to the appropriate bromide of Formula XVII by known brominating methods and then treated with an excess of potassium cyanide in dimethylformamide at about 70° C. to produce the nitriles of Formula XVIII. Conversion of the nitrile moiety to the tetrazoles of Formula XIX is preferably accomplished with tri-n-butyltin azide following the general procedures described by J. L. Kraus in Syn. Comm., (1986), 16. 827.

Reaction Scheme 4

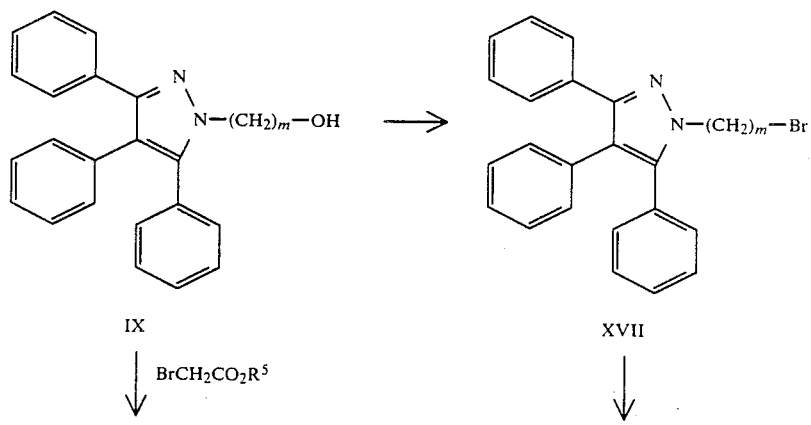

Reaction Scheme 4 -continued

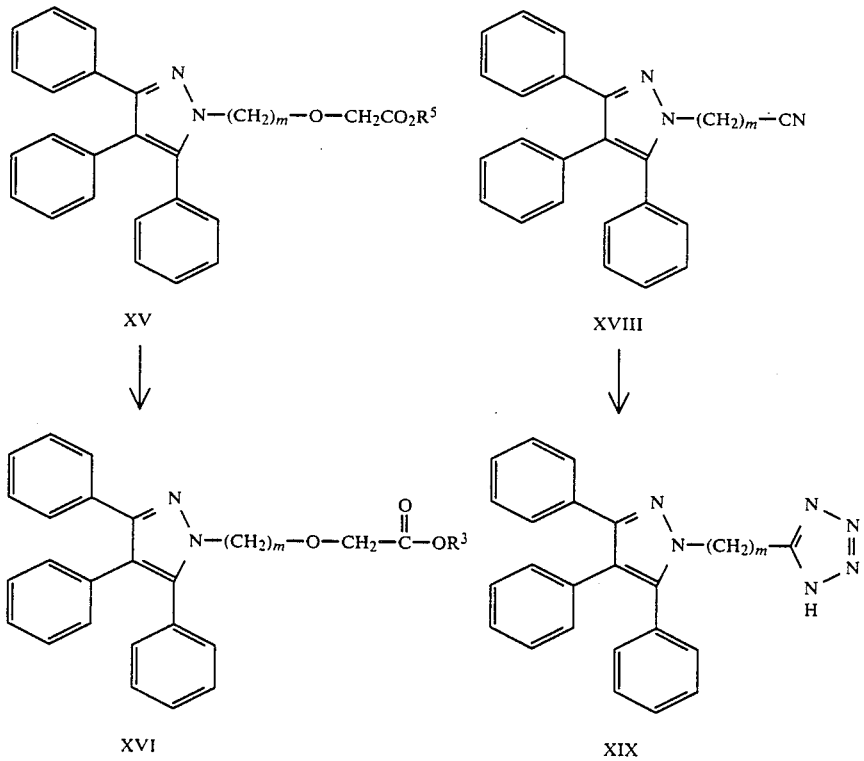

The introduction of a heteroatom in the side chain of Formula I wherein Z is O, S, SO and SO$_2$ may be incorporated in the compounds of Formula I by the synthetic sequences delineated in Reaction Schemes 4 and 5.

The compounds of Formula I, and specifically the compounds wherein Z is oxygen and n is 1, as illustrated in Reaction Scheme 4, may be prepared by alkylation of the alcohols of Formula IX with, for example, t-butyl-bromoacetate under phase-transfer conditions similar to those described by W. Skuballa et al. in *J. Med. Chem.*, 1986, 29, 313 to provide the esters of Formula XV which may readily be converted to the acids of Formula XVI wherein R$^3$ is hydrogen upon dissolution in trifluoroacetic acid or to pharmaceutically acceptable salts thereof.

The compounds of Formula I, wherein Z is S, SO and SO$_2$, may be prepared by the reactions illustrated in Reaction Scheme 5. Specifically, in the instance wherein n is 1, the bromoalkyl of Formula XVII is treated with methylmercaptoacetate in the presence of a base to furnish the esters of Formula XX which may optionally be hydrolyzed under basic conditions to the acids of Formula XXI or pharmaceutically acceptable salts thereof. If desired, the sulfides of Formula XX may be oxidized to the sulfoxides of Formula XXII or the sulfones of Formula XXIV with standard sulfur oxidizing agents well-known to those skilled in the art such as Oxone which is a potassium peroxymonosulfate complex as described by B. M. Trost and D. D. Curran in *Tetrahedron Letters*, 1981, 22. 1287 or sodium periodate.

The preparation of the sulfoxides of Formula XXII from the sulfides of Formula XX may preferably be carried out with a slight molar excess of Oxone in aqueous methanol at a temperature of about $-10°$ C.

Reaction Scheme 5
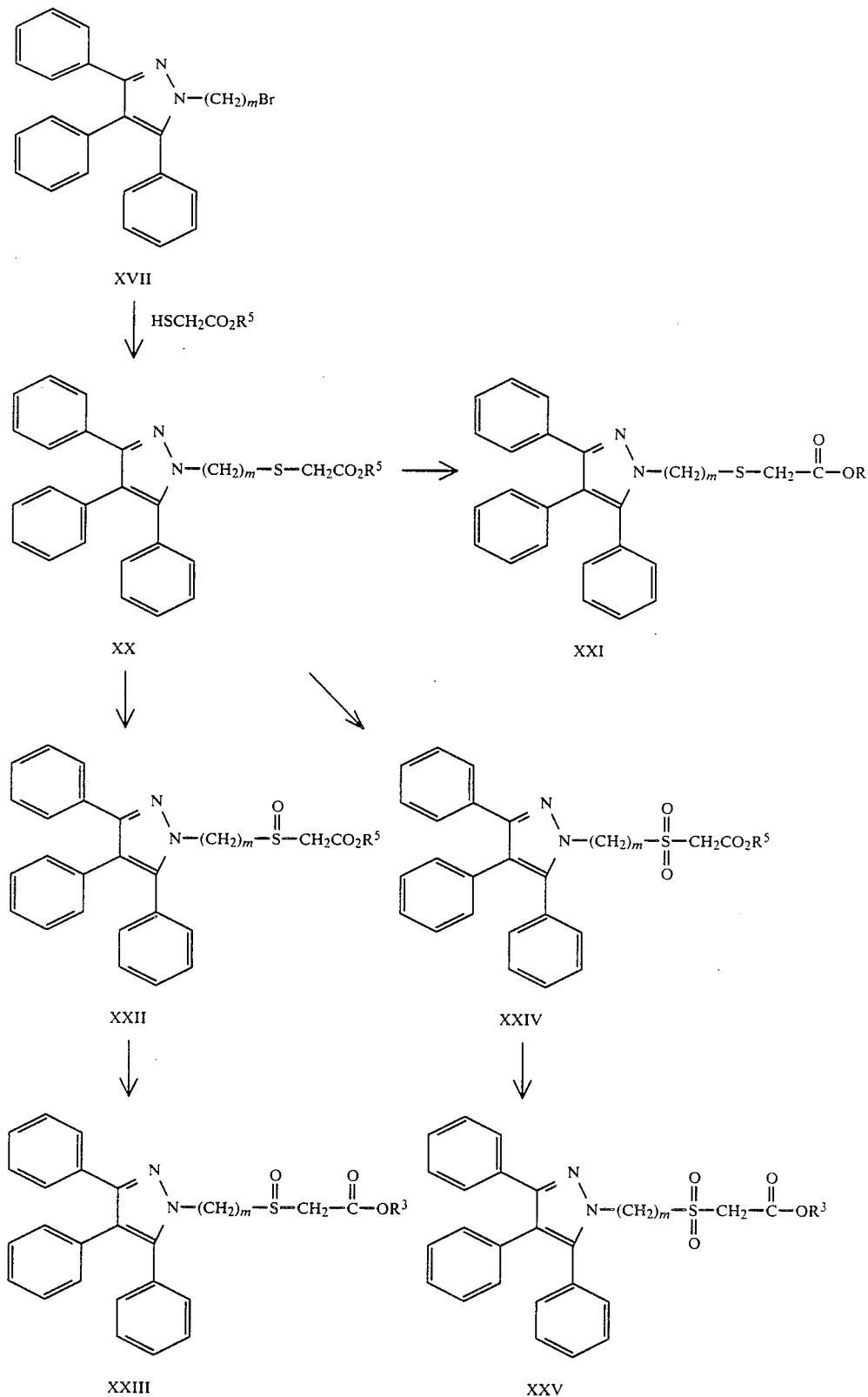
However, when it is desired to prepare the sulfones of Formula XXIV, the oxidation is preferably conducted with a three-fold excess of oxidant, e.g., Oxone at about room temperature. Alternatively, it is understood by those skilled in the art that the sulfoxides of Formula XXII may also be converted to the sulfones of Formula XXIV with the use of additional oxidant. Furthermore, the sulfoxides and sulfones of Formulas XXII and XXIV may be converted to their corresponding acids of Formulas XXIII and XXV, respectively, under alkaline conditions.

cetal at 110° C. as described by Z. Arnold and M. Komilov in *Coll. Czech. Chem. Comm.*, 1964, 29, 645, to give the enaminone of Formula XXVII, then treatment with hydrazine to furnish the pyrazole of Formula XXVIII in 90% overall yield.

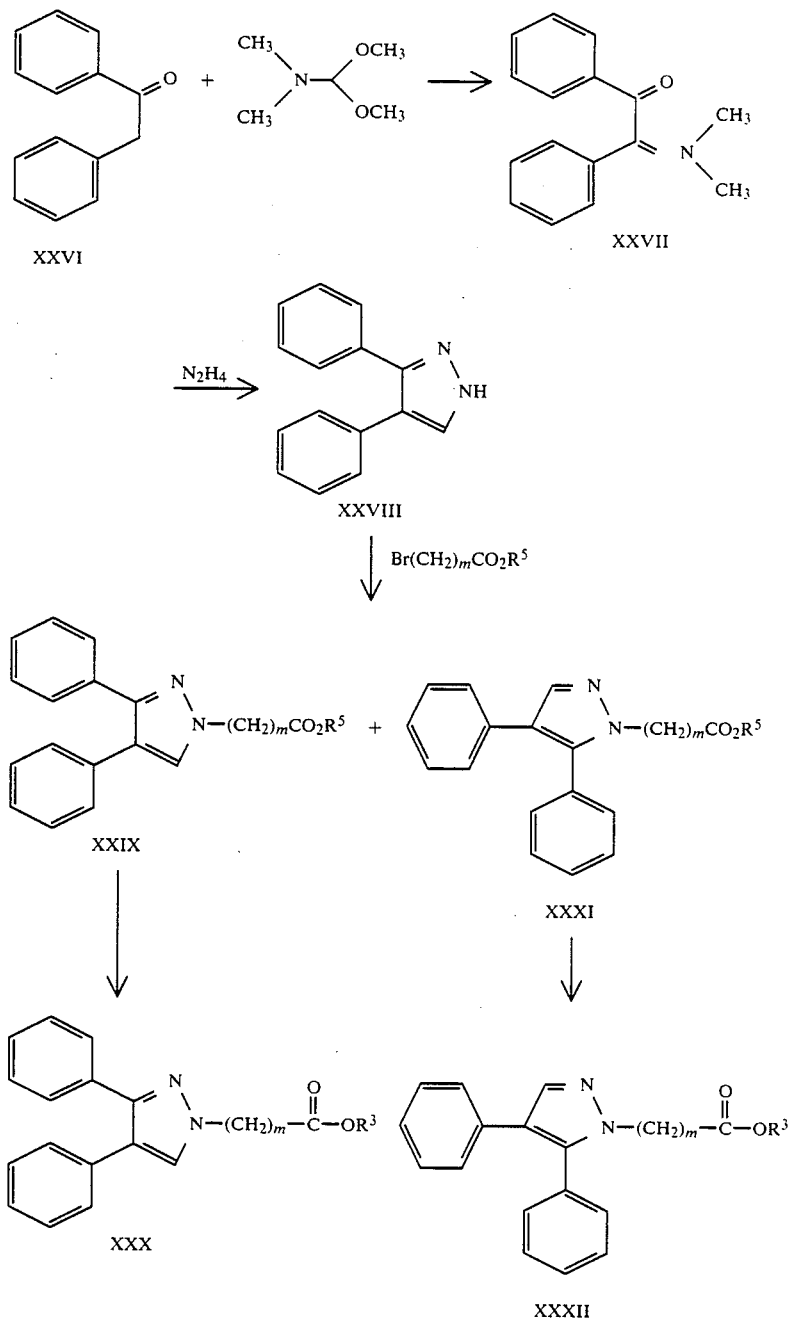

Reaction Scheme 6

The preparation of unsymmetrically-substituted pyrazoles of Formula I, wherein $R^1$ or $R^2$ is phenyl is illustrated in Reaction Scheme 6 and may be prepared from the known starting material diphenylpyrazole of Formula XXVIII which is described by W. Wislicenus and A. Ruthing in *Annalen*, 1911, 379, 229. However, an improved procedure for the preparation of diphenylpyrazole was developed which entailed treatment of the deoxybenzoin of Formula XXVI with DMF-dimethyla- The diphenylpyrazole of Formula XXVIII may then be alkylated with various alkylating agents by methods well-known to those skilled in the art. Thus, the pyrazole of Formula XXVIII may be treated with a strong base such as sodium hydride in a non-reactive solvent, e.g., toluene, tetrahydrofuran and N,N-dimethylformamide or mixture thereof at a temperature from −30° C.

to about 50° C. and then with an alkylating agent such as methyl 9-bromononanoate. The temperature is not critical and will usually depend on the alkylating agent employed. This non-specific alkylation produces a mixture of regioisomers which may be separated by conventional procedures such as crystallization or chromatography to give the desired 3,4-diphenylpyrazole of Formula XXIX and 4,5-diphenylpyrazole of Formula XXXI. Subsequent alkaline hydrolysis of the esters of Formulas XXIX and XXXI will produce the acids of Formulas XXX and XXXII, respectively and, if desired, their corresponding pharmaceutically acceptable salts.

As stated above, the compounds of Formula I or pharmaceutically acceptable salts thereof have pharmacological properties which make them particularly useful as inhibitors of blood platelet aggregation and as antihyperlipidemic agents.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few and in ischaemic heart disease, artherosclerosis, multiple sclerosis, intracranial tumors, thromboembolism, and hyperlipemia; refer to A. Poplawski, et al., *J. Artherosclerosis Research*, 8, 721 (1968). Thus, the compounds of the invention which have antithrombogenic (inhibit blood platelet aggregation) are useful in prevention or treatment of conditions involving platelet aggregation and thrombosis such as the above. The instant compounds are also considered to have antimetastatic potential in view of their platelet inhibition properties.

The pharmacological properties of the instant compounds can be demonstrated by conventional in vitro and in vivo biological tests such as the following.

IN VITRO INHIBITION OF HUMAN PLATELET AGGREGATION

The aggregometer method of Born, C. V. R., *J. Physiol.*, (London), 1962, 162, 67–68, as modified by Mustard, J. F., et al., *J. Lab. Clin. Med.* 1964, 64, 548–599 was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140 xg) from citrated (3.8%) human blood. All glassware used for preparation of PRP is silicon treated. ADP in final concentration of 0.5 mcg/mL or 0.05 mL of a collagen suspension prepared according to the method described by Evans, G., et al., *J. Exp. Med.* 1968, 128, 877–894 was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Inhibitor Concentration IC$_{50}$) values calculated. In this test, the IC$_{50}$ values for dipyridamole, a clinically useful antithrombogenic agent, are >512 mcg/ml vs. ADP and 245 mcg/ml vs collagen. Results are given in Table I hereinafter for various Formula I compounds.

TABLE I

| | Inhibition of Platelet Aggregation IC$_{50}$ ($\mu$g/mL) - Human PRP | |
|---|---|---|
| Example | vs:ADP | vs. Collagen |
| 4 | 0.2 | 0.096 |
| 8 | 1.9 | |
| 10 | 0.35 | 0.12 |
| 14 | 2.0 | 0.27 |
| 15 | 0.16 | 0.068 |
| 17 | 1.5 | |
| 18 | 2.5 | 0.45 |
| 21 | 0.41 | 0.15 |
| 25 | 3.2 | |
| 27 | 1.9 | 0.16 |
| 36 | 3.5 | |
| 40 | 0.5 | 0.052 |
| 44 | 0.6 | |

IN VIVO INHIBITION OF BIOLASER INDUCED THROMBOSIS

The laser induced thrombosis method is a modification of the technique developed by Sanders, A. G., et al. in *Brit. J Exp. Pathol.*, 1954, 35, 331 and Grant, L., et al. in *Proc. Soc. Exp. Biol. Med.*, 1965, 119, 1123. A detailed description of this method has been described by Fleming, J. S., et al., in *Platelets and Thrombosis*, A. Scriabine and S. Sherry, eds., Baltimore, Univ. Park Press, pp. 247–262, 1974 and is hereby incorporated by reference.

Briefly, Lucite ear chambers were chronically implanted in adult, English lop-ear rabbits. The animals were conditioned to lie quietly in the supine position. Localized microvascular injury was induced by focusing a single ruby laser beam through a microscope into the lumen of a vessel 10–60 $\mu$M in diameter. This evoked the formation of a small thrombus consisting of platelets accumulated around a core of one or two damaged red cells. Thrombus area was determined as a product of two perpendicular measurements made by using a micrometer eye piece. The mean thrombus area ($\mu$M$^2$) obtained for 10 trials in each rabbit served as a control value. The test compound was administered orally and post-dose trials were performed at selected times. Pharmacological activity was evaluated by comparing pre- and post-dose mean thrombus areas.

In the above biolaser model of thrombosis, the compound of Example 15 exhibited over 60% inhibition of thrombus formation at oral doses of 10 and 30 mg/kg while an oral dose of 1 mg/kg produced approximately 30% inhibition.

In still another embodiment, this invention includes pharmaceutical compositions comprising at least one compound of Formula I in combination with a pharmaceutical carrier or diluent.

In another embodiment, this invention relates to a therapeutic method for the treatment of hypercholesterolemia and/or hyperlipoproteinemia in a mammal in need thereof, which comprises administering to said mammal a therapeutically effective amount of a compound of Formula I or a pharmaceutically acceptable salt thereof.

In yet another embodiment, this invention relates to a therapeutic method for inhibiting blood platelet aggregation in a mammal in need thereof, which comprises administering to said mammal a therapeutically effective amount of a compound of Formula I or a pharmaceutically acceptable salt thereof.

The dosage employed in the instant therapeutic methods will vary with the form of administration, the particular compound chosen, the subject being tested and the effect desired. Suitable effective doses in animals range from 0.1-50 mg/kg body weight orally and from 0.05-10 mg/kg body weight parenterally (generally characterized as subcutaneous, intramuscular, and intravenous injection). It is contemplated that the effective unit dose in man will range from 0.1 to 30 mg and preferably from 0.5 to 20 mg administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate) Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Thomas-Hoover capillary melting point apparatus and are uncorrected. Proton magnetic resonance ($^1$H NMR) spectra were recorded on a Bruker AM 300, Bruker WM 360 or Varian T-60 CW spectrometer. All spectra were determined in $CDCl_3$ or $DMSO-d_6$ unless otherwise indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; and dd, doublet of doublet. Infrared (IR) spectra were determined on a Nicolet MX-1 FT spectrometer from 4000 $cm^{-1}$ to 400 $cm^{-1}$, calibrated to 1601 $cm^{-1}$ absorption of a polystyrene film and are reported in reciprocal centimeters ($cm^{-1}$). Mass spectra were recorded on a Kratos MS-25 instrument utilizing the fast atom bombardment (FAB) technique or on a Finnigan 4500 instrument utilizing the EI or CI technique. The mass data are expressed in the format: parent ion ($M^+$) or protonated ion ($MH^{30}$). All evaporations of solvents were performed under reduced pressure. Oxone is a registered trademark of the DuPont Company for potassium peroxymonosulfate complex.

EXAMPLE 1

Ethyl 3,4,5-triphenyl-1H-pyrazol-1-hexanoate

Sodium hydride (1.30 g of 60% dispersion, 32 mmol) was washed twice with hexane and covered with dimethylformamide (DMF) (100 mL). 3,3,5-Triphenyl-3H-pyrazole (8 g, 27 mmol) was added and the mixture stirred at 110° C. under an atmosphere of nitrogen for 25 minutes before being cooled to room temperature. Ethyl 6-bromohexanoate (6.6 g, 5.3 mL, 29 mmol) in DMF (2 mL) was added dropwise and the mixture stirred at room temperature. After 15 minutes water was added and the mixture extracted with diethyl ether (4 times). The combined extracts were washed with water (3 times), dried and concentrated in vacuo to give an oil. Chromatography on a column of silica gel using a mixture of hexane and diethyl ether (11:9) as eluent afforded ethyl 3,4,5-triphenyl-1H-pyrazol-1-hexanoate (11.83 g, 100%) as a viscous oil. MS(CI): m/e =439 ($MH^+$).

IR (film) $v_{max}$: 1740 ($CO_2R$) $cm^{-1}$.

$^1H$ NMR ($CDCl_3$) $\delta$:1.21 (3H, t, J =6.5 Hz, $OCH_2CH_3$), 1.29 (2 H, quintet, J =7.5 Hz, $CH_2$), 1.56 (2 H, quintet, J =7.5 Hz, $CH_2$), 1.87 (2 H, quintet, J =7.5 Hz, $CH_2$), 2.23 (2 H, t, J =7.5 Hz, $CH_2CO_2Et$), 4.00-4.20 (4 H, m, $OCH_2CH_3$ and $N-CH_2$), 7.00-7.60 (15 H, m, aromatic H).

Anal. Calcd. for $C_{29}H_{30}N_2O_2$:
C,79,42; H, 6,90; N, 6.39;
Found: C, 79.35; H, 6.93; N, 6.52.

EXAMPLE 2

3,4,5-Triphenyl-1H-pyrazol-1-hexanol

A solution of ethyl 3,4,5-triphenyl-1H-pyrazol-1-hexanoate (9 g, 20 mmol) in diethyl ether (30 mL) was added dropwise to a stirred suspension of lithium aluminum hydride (780 mg, 20 mmol) in diethyl ether (220 mL). After 15 minutes, water was cautiously added dropwise until the salts collected. The ethereal layer was decanted, the residue washed several times with diethyl ether and the combined extracts dried over sodium sulfate and evaporated to give a viscous oil (8.13 g, 100%) that slowly solidified. An 800 mg sample was recrystallized from a mixture of hexane and diethyl ether to give 3,4,5-triphenyl-1H-pyrazol-1-hexanol (700 mg); m.p. =76°-78° C. MS(CI): m/e =397 (MH+).

IR (KBr) $\nu_{max}$:3200 (OH) cm$^{-1}$.

$1_H$ NMR (CDCl$_3$) δ: 1.15–1.40 (4 H, m, CH$_2$), 1.47 (2 H, quintet, J =6.5 Hz, CH$_2$), 1.60 (1 H, t, J =5 Hz, OH), 1.83 (2 H, m, CH$_2$), 3.54 (2 H, q, J =6 Hz, CH$_2$OH), 4.07 (2 H, t, J =7 Hz, N-CH$_2$), 6.90–7.60 (15 H, m, aromatic H).

Anal Calcd. for C$_{27}$H$_{28}$N$_2$)O: C, 81.78; H, 7.12; N, 7.07

Found: C, 81.75; H, 7.14; N, 7.00.

EXAMPLE 3

1,1-Dimethylethyl [[6-(3,4,5-triphenyl-1H-pyrazol-1-yl)-hexyl]oxy]acetate

A mixture of 3,4,5-triphenyl-1H-pyrazol-1-hexanol (5 g, 12 mmol), tert-butyl bromoacetate (4.92 g, 4.10 mL, 25 mmol), tetrabutylammonium hydrogen sulfate (0.4 g), 50% aqueous sodium hydroxide solution (80 mL) and toluene (80 mL) was stirred vigorously at room temperature. After 18 hours, the reaction mixture was diluted with water (100 mL), the organic layer separated and the aqueous layer extracted twice with diethyl ether. The combined extracts were dried over sodium sulfate and the solvent evaporated to give an oil which was chromatographed on a column of silica gel. Elution with a mixture of hexane and diethyl ether (2:1) afforded 1,1-dimethylethyl [[6-(3,4,5-triphenyl-1H-pyrazol-1-yl)hexyl]oxy]acetate (5.84 g, 95%) as an oil that slowly crystallized to a white solid; m.p. =69°-72° C. MS(CI): m/e =511 (MH+).

IR (KBr) $\nu_{max}$:1750 (CO$_2$R), 1140 (C—O—C) cm$^{-1}$ $1_H$ NMR (CDCl$_3$) δ:1.24 (4 H, m, (CH$_2$)$_2$), 1.46 (9H, s, C(CH$_3$)$_3$), 1.53 (2 H, m, CH$_2$), 1.88 (2 H, m, CH$_2$), 3.44 (2 H, t, J=6.5 Hz, OCH$_2$CH$_2$), 3.91 (2 H, s, OCH$_2$CO$_2$R), 4.07 (2 H, t, J =7 Hz, N-CH$_2$), 6.90–7.50 (15 H, m, aromatic H).

Anal. Calcd. for C$_{33}$H$_{38}$N$_2$O$_3$:
C, 77.62; H, 7.50; N, 5.49;
Found: C, 77.55; H, 7.62; N, 5.45.

EXAMPLE 4

[[6-(3,4,5-Triphenyl-1H-pyrazol-1-yl)hexyl]oxy]acetic acid 1,1-dimethylethyl [[6-(3,4,5-triphenyl-1H-pyrazol-1-yl)hexyl]oxy]acetate (4.30 g, 8 mmol) was dissolved in trifluoroacetic acid (25 mL). After stirring at room temperature for 40 minutes, the volatiles were removed to leave an oily residue which was dissolved in diethyl ether and diluted with hexane. [[6-(3,4,5-Triphenyl-1H-pyrazol-1-yl)hexyl]oxy]acetic acid (3.20 g, 83%) was collected by filtration; m.p. =92°-94° C. MS(CI): m/e =455 (MH$^{30}$ ).

IR (KBr) $\nu_{max}$:1740 (CO$_2$H), 1140 (C—O—C) cm$^{-1}$.

$1_H$ NMR (CDCl$_3$) δ:1.12 (4 H, m, CH$_2$), 1.55 (2 H, quintet, J=7 Hz, CH$_2$), 1.83 (2 H, quintet, J =7 Hz, CH$_2$), 3.47 (2 H, t, J=6.5 Hz, OCH$_2$CH$_2$, 4.04 (2 H, s, OCH$_2$CO$_2$H , 4.10 (2 H, t, J=7 Hz, N-CH$_2$), 6.95–7.55 (15 H, m, aromatic H), 8.93 (1 H, bs, CO$_2$ H).

Anal. Calcd. for C$_{29}$H$_{30}$N$_2$O$_3$: C, 76.63; H, 6.65; N, 6.16;

Found: C, 76.66; H, 6.62; N, 6.09.

EXAMPLE 5

3,4,5-Triphenyl-1H-pyrazol-1-nonamide

Oxalyl chloride (0.42 g, 0.29 mL, 3.3 mmol) was added dropwise to a solution of 3,4,5-triphenyl-1H-pyrazol-1-nonanoic acid (1 g, 2.2 mmol) in dry tetrahydrofuran (THF) (15 mL) containing a catalytic amount of DMF maintained at 0° C. under an atmosphere of nitrogen. After 30 minutes the mixture was warmed to room temperature, stirred for 30 minutes and then concentrated in vacuo to give a yellow solid which was dissolved in THF (10 mL). Concentrated ammonium hydroxide solution (specific gravity 0.90, 2 mL) was added dropwise at room temperature and the mixture stirred for 20 minutes before being poured onto water and extracted with dichloromethane. The combined extracts were dried over sodium sulfate and the solvent evaporated to leave a white solid. Recrystallization from a mixture of dichloromethane and hexane gave 3,4,5-triphenyl-1H-pyrazol-1-nonamide (0.80 g, 80%); m.p. =104°-107° C. MS(CI): m/e =452 (MH$^{30}$ ).

IR (KBr) $\nu_{max}$:1655 (CONH$_2$) cm$^{-1}$.

$1_H$ NMR (CDCl$_3$) δ:1.00–1.20 (8H, bs, CH$_2$), 1.57 (2 H, quintet, J =7 Hz, CH$_2$), 1.83 (2 H, q, J =7 Hz, CH$_2$), 2.15 (2 H, t, J =7 Hz, CH$_2$CONH) 4.05 (2 H, t, J =7 Hz, N-CH$_2$), 5.52–5.72 (2 H, bs, NH$_2$), 6.90–7.70 (15 H, m, aromatic H).

Anal. Calcd. for C$_{30}$H$_{33}$N$_3$O: C, 79.79; H, 7.37; N, 9.31;

Found: C, 79.46; H, 7.50; N, 9.35.

EXAMPLE 6

N-(Methylsulfonyl)-3,4,5-triphenyl-1H-pyrazol-1-nonamide

A mixture of 1,1-carbonyldiimidazole (394 mg, 2.4 mmol) and 3,4,5-triphenyl-1H-pyrazol-1-nonanoic acid (1 g, 2.2 mol) in THF (10 mL) was stirred at room temperature under an atmosphere of nitrogen. After 30 minutes, the mixture was heated to reflux temperature for 30 minutes before being cooled to room temperature. Methanesulfonamide (210 mg, 2.2 mmol) was added, followed (after 10 minutes) by a solution of 1,8-diazabicyclo[5.4.0]undec-7-ene (336 mg, 0.34 mL, 2.2 mmol) in THF (5 mL). The mixture was stirred at room temperature for 16 hours, poured onto 2 N hydrochloric acid solution and extracted with dichloromethane. The combined extracts were dried over sodium sulfate and concentrated to give an oil. Chromatography on a column of silica gel using a mixture of diethyl ether and hexane (4:1) as eluent furnished N-(methylsulfonyl)-3,4,5-triphenyl-1H-pyrazol-1-nonamide (1 g, 80%) as a white solid; m.p. =88°-90° C. MS(CI): m/e=530 (MH+).

IR (KBr) $\nu_{max}$:1720 (CONSO$_2$CH$_3$) cm$^{-1}$.

$1_H$ NMR (CDCl$_3$) δ:1.22 (8H, m, CH$_2$), 1.54 (2 H, quintet, J =7 Hz, CH$_2$), 1.84 (2 H, quintet, J =7 Hz, —CH$_2$—), 2.18 (2 H, t, J =7.5 Hz, CH$_2$·CO), 3.21 (3H, s, SO$_2$CH$_3$), 4.08 (2 H, t, J =7.5 Hz, N-CH$_2$), 6.90–7.60 (15 H, m, aromatic H), 9.64 (1 H, bs, NHSO$_2$).

Anal. Calcd. for C$_{31}$H$_{35}$N$_3$O$_3$S:
C, 70.29; H, 6.66; N, 7.93;
Found: C, 70.21; H, 6.70; N, 7.83.

EXAMPLE 7

Ethyl 3,4,5-triphenyl-1H-pyrazol-1-octanoate hemihydrate

Sodium hydride (0.58 g of a 50% dispersion, 12 mmol) was washed twice with hexane and covered with DMF (45 mL). 3,3,5-Triphenyl-3H-pyrazole (3 g, 10 mmol) was added and the mixture heated at 110° C. under nitrogen for 45 minutes before being cooled to room temperature. A solution of ethyl 8-bromo-octanoate (2.80 g, 11 mmol) in DMF (2 mL) was added and the mixture stirred for 10 minutes before being poured onto a mixture of water and ethyl acetate. The aqueous layer was discarded and the organic layer washed twice with water and once with saturated sodium chloride solution. The organic phase was dried over sodium sulfate and concentrated to afford an oil. Chromatography on a column of silica gel using a mixture of hexane and ethyl acetate (17:3) as eluent gave ethyl 3,4,5-triphenyl-1H-pyrazol-1-octanoate hemihydrate (4.05 g, 85%) as an oil. MS(CI): m/e =467 (MH+).

IR (film) $\nu_{max}$:1740 ($CO_2R$) $cm^{-1}$.

$1_H$ NMR ($CDCl_3$) δ: 1.05–1.20 (9H, m, $CH_2 + CH_3$), 1.57 (2 H, t, J=7.5 Hz, $CH_2$), 1.84 (2 H, t, J =7.5 Hz, $CH_2$), 2.23 (2 H, t, J =7.5 Hz, $CH_2CO_2R$, 4.00–4.20 (4 H, m, N-$CH_2$ and $OCH_2$), 6.95–7.60 (15 H, m, aromatic H).

Anal. Calcd. for $C_{31}H_{34}N_2O_2 \cdot 0.5H_2O$:
C, 78.29; H, 7.42; N, 5.90; H20, 1.90;
Found: C, 77.95; H, 7.50; N, 5.36; H20, 1.64.

EXAMPLE 8

3,4,5-Triphenyl-1H-pyrazol-1-octanoic acid hydrate

A mixture of ethyl 3,4,5-triphenyl-1H-pyrazol-1-octanoate (3 g, 6.4 mmol), 3 N aqueous sodium hydroxide solution (6.4 mL, 19 mmol) and methanol (40 mL) was heated on a steam bath for 25 minutes before being cooled and concentrated in vacuo. The residue was diluted with water (25 mL) and 2 N hydrochloric acid solution added until pH =1. The mixture was extracted with dichloromethane and the combined extracts washed with water and saturated NaCl solution before being dried over sodium sulfate. Removal of the solvent left an oil that slowly crystallized. Recrystallization from a mixture of hexane and dichloromethane (2:1) afforded 3,4,5-triphenyl-1H-pyrazol1-octanoic acid hydrate (1.19 g, 42%); m.p. =97.5°–99.5° C. MS(CI): m/e =439 (MH+).

IR (KBr) $\nu_{max}$:1710 ($CO_2O$) $cm^{-1}$.

$1_H$ NMR ($CDCl_3$) δ: 1.15–1.45 (6H, m, $CH_2$), 1.50–1.70 (2 H, m, $CH_2$), 1.70–1.95 (2 H, m, $CH_2$), 2.29 (2 H, t, J =7 Hz, $CH_2CO_2H$), 4.07 (2 H, t, J =7 Hz, $NCH_2$), 6.90–7.55 (15 H, m, aromatic H).

Anal Calcd. for $C_{29}H_{30}N_2O_2 \cdot 0.5H_2O$:
C, 79.26; H, 6.91; N, 6.38; $H_2O$, 0.20;
Found: C, 78.98; H, 6.86; N, 6.33; $H_2O$, 0.12.

EXAMPLE 9

3,4,5-Triphenyl-1H-pyrazol-1-butanal 3,4,5-Triphenyl-1H-pyrazol-1-butanol (4 g, 10.9 mmol) in dry $CH_2Cl_2$ (10 mL) was added to a stirred suspension of pyridinium chlorochromate (7.03 g, 32.6 mmol) in dry $CH_2Cl_2$ (370 mL). After 3 hours, the $CH_2Cl_2$ was removed in vacuo and the residue diluted with diethyl ether (800 mL) and filtered through diatomateous earth. The organic phase was washed twice with water and once with saturated sodium chloride solution, dried over sodium sulfate and concentrated to furnish 3,4,5-triphenyl-1H-pyrazol-1-butanal as a viscous oil. MS(CI): m/e =367 (MH+)

$1_H$ NMR ($CDCl_3$) δ:2.12 (2 H, quintet, J =7.5 Hz, $CH_2$), 2.45 (2 H, t, J =7.5 Hz, $CH_2CO$), 4.12 (2 H, t, J =7.5 Hz, N-$CH_2$), 6.95–7.55 (15 H, m, aromatic H), 9.62 (1H, s, CHO).

EXAMPLE 10

(Z) and (E)-9-(3,4,5-Triphenyl-1H-pyrazol-1-yl)-5-nonenoic acid hydrate n-Butyllithium (7.1 mL of 2.5 M solution in hexane, 17.7 mmol) was added dropwise to a solution of hexamethyldisilazane (2.86 g, 17.7 mmol) in anhydrous THF (70 mL) maintained at 5° C. under an atmosphere of nitrogen. After 15 minutes, the cooling bath was removed and (4-carboxybutyl)triphenylphosphonium bromide (3.92 g, 8.8 mmol) added. The mixture was stirred for 55 minutes to give a red solution before adding 3,4,5-triphenyl-1H-pyrazol-1-butanal (2.44 g, 8.0 mmol) in THF (40 mL). After 45 minutes, the reaction mixture was diluted with ethyl acetate (400 mL) and extracted with water (3 times). The aqueous layer was acidified to pH =1 with 2 N hydrochloric acid solution and extracted with dichloromethane (3 times). The combined extracts were dried over sodium sulfate, concentrated in vacuo and the residue chromatographed on a column of silica gel using a mixture of ethyl acetate and hexane (11:9) as eluent. Elution gave a 3:1 mixture of (Z) and (E)-9-(3,4,5-triphenyl-1H-pyrazol-1-yl)-5-nonenoic acid hydrate (2 g, 55%) as a colorless oil. MS(CI): m/e =451 (MH+).

IR (KBr) $\nu_{max}$:1710 ($CO_2$ H) $cm^{-1}$.

$1_H$ NMR ($CDCl_3$) δ:1.66 (2 H, m, $CH_2$), 1.80–2.20 (6H, m, $CH_2$), 2.30 (2 H, t, J =7.5 Hz, $CH_2CO_2$ H), 4.10 (2 H, t, J =7.5 Hz, N-$CH_2$), 5.25–5.40 (2 H, m, vinylic H), 6.90–7.60 (15 H, m, aromatic H), 9.96 (1 H, bs, $CO_2$ H).

Anal. Calcd. for $C_{30}H_{30}N_2O_2 \cdot 0.4 H_2O$:
C, 78.72; H, 6.79; N, 6.12; $H_2O$, 1.57;
Found: C, 78.70; H, 6.68; N, 6.45; $H_2O$, 2.63.

EXAMPLE 11

Methyl 9-(3,4,5-triphenyl-1H-pyrazol-1-yl)-5-nonenoate

A solution of (Z) and (E)-9-(3,4,5-triphenyl-1H-pyrazol-1-yl)-5-nonenoic acid (3:1), (850 mg, 1.9 mmol) and concentrated sulfuric acid (2 drops) in methanol (75 mL) was heated at reflux for 1.5 hours. The solvent was evaporated, the residue dissolved in $CH_2Cl_2$, washed with water and saturated sodium chloride solution before being dried over sodium sulfate. Evaporation of the solvent left an oil which was chromatographed on a column of silica gel. Elution with a mixture of hexane and ethyl acetate (17:3) containing 1% triethylamine gave methyl 9-(3,4,5-triphenyl-1H-pyrazol-1-yl)-5-nonenoate as a 3:1 ratio of (Z) to (E) geometrical isomers. MS(CI): m/e =465 (MH+).

IR (film) $\nu_{max}$:1720 ($CO_2R$) $cm^{-1}$.

$1_H$ NMR ($CDCl_3$) δ:1.58 (2 H, m, $CH_2$), 1.80–2.10 (6H, m, $CH_2$), 2.25 (2 H, m, $CH_2$), 3.62 (3H, s, $CO_2CH_3$), 4.07 (2 H, t, J =7 Hz, N-$CH_2$), 5.20–5.40 (2 H, m, vinylic H), 6.90–7.50 (15 H, m, aromatic H).

Anal. Calcd. for $C_{31}H_{32}N_2O_2$:
C, 80.15; H, 6.95; N, 6.03;
Found: C, 79.92; H, 7.08; N, 6.12.

EXAMPLE 12

(Z) and (E)-11-(3,4,5-Triphenyl-1H-pyrazol-1-yl)-5-undecenoic acid hydrate

A procedure analogous to that described in Example 9 and 10 except that 3,4,5-triphenyl-1H-pyrazol-1-butanol utilized therein was replaced by 3,4,5-triphenyl-1H-pyrazol-1-hexanol and there was thereby produced a mixture of (Z):(E)-11-(3,4,5-triphenyl-1H-pyrazol-1-yl)-5-undecenoic acid hydrate (4.83 g, 55%) as a clear colorless oil which was isolated after chromatography using hexane/ethyl acetate (11:9) as eluent. MS(CI): m/e =479 (MH+).

IR (film) $\nu_{max}$:1715 ($CO_2$ H) cm$^{-1}$.

$1_H$ NMR (CDCl$_3$) δ: 1.05–1.40 (4 H, m, CH$_2$), 1.68 (2 H, quintet, J =7 Hz, CH$_2$), 1.75–2.20 (6H, m, CH$_2$), 2.30 (2 H, m, CH$_2$), 4.11 (2 H, t, J =7.5 Hz, N-CH$_2$), 5.20 and 5.50 (2 H, m, vinylic H), 6.90–7.60 (15 H, m, aromatic H), 11.05 (1 H, bs, CO$_2$ H).

Anal. Calcd. for $C_{32}H_{34}N_2O_2 \cdot 0.2 H_2O$:
C, 79.71; H, 7.20; N, 5.81; H$_2$O, 0.75;
Found: C, 79.73; H, 7.18; N, 5.98; H$_2$O, 2.94.

EXAMPLE 13

3,4,5-Triphenyl-1H-pyrazol-1-undecanoic acid

A mixture of 11-(3,4,5-triphenyl-1H-pyrazol-1-yl)-5-undecenoic acid (2.3:1 (Z):(E)) (2.53 g, 5.3 mmol), 10% palladium on carbon (0.5 g) and methanol (250 mL) was hydrogenated at 35 psi on a Parr hydrogenation apparatus for 1 hour. The mixture was filtered through diatomateous earth and the solvent removed to leave a viscous oil which slowly solidified to an amorphous solid, 3,4,5-triphenyl-1H-pyrazol-1-undecanoic acid (2.29 g, 90%); m.p. =81.5°-84° C. MS(CI): m/e =481 (MH+).

IR (KBr) $\nu_{max}$:1730 ($CO_2$ H) cm$^{-1}$.

$1_H$ NMR (CDCl$_3$) δ: 1.05–1.45 (16H, m, CH$_2$), 1.59 (2 H, quintet, J =6.5 Hz, CH$_2$), 2.30 (2 H, t, J =7 Hz, CH$_2$), 4.08 (2 H, t, J =7 Hz, N-CH$_2$), 6.95–7.70 (15 H, m, aromatic H), 9.28 (1 H, bs, CO$_2$ H).

Anal. Calcd for $C_{32}H_{36}N_2O_2$: C, 79.97; H, 7.55; N, 5.83;
Found: C, 80.08; H, 7.58; N, 5.69.

EXAMPLE 14

Methyl 3,4,5-triphenyl-1H-pyrazol-1-nonanoate

Sodium hydride (588 mg of a 60% dispersion in mineral oil, 13 mmol) was washed twice with hexane and covered with dimethylformamide (DMF), (45 mL). 3,3,5-Triphenyl-3H-pyrazole (3 g, 10 mmol) was added and the mixture stirred at 110° C. under a nitrogen atmosphere for 30 minutes before being cooled to room temperature. Methyl 9-bromononanoate (2.80 g, 11 mmol) in DMF (2 mL) was added dropwise, the mixture stirred at room temperature for 2 hours and then poured onto water (100 mL). The mixture was extracted with diethyl ether (3×100 mL), the extracts washed with water (3×100 mL), dried over sodium sulfate and concentrated to give an oil. Chromatography on a column of silica gel using a mixture of hexane and diethyl ether (2:1) as eluent afforded methyl 3,4,5-triphenyl-1H-pyrazol-1-nonanoate (4.72 g, 100%) as a viscous oil. (MS(CI): m/e =467 (MH+).

IR (KBr) $\nu_{max}$:1740 (CO$_2$CH$_3$) cm$^{-1}$.

$1_H$ NMR (CDCl$_3$) δ:1.06 (8H, bs, —CH$_2$), 1.41 (2 H, t, J =7 Hz, CH$_2$), 1.68 (2H, bs, CH$_2$), 2.11 (2H, t, J =7.5 Hz CH$_2$CO$_2$), 3.47 (3H, s, CO$_2$CH$_3$) 3.90 (2 H, t, J =7 Hz, N-CH$_2$), 6.83–7.32 (15 H, m, aromatic H).

Anal. Calcd. for $C_{31}H_{34}N_2O_2$:
C, 79.80; H, 7.34; N, 6.00;
Found: C, 79.99; H, 7.51; N, 6.31.

EXAMPLE 15

3,4,5-Triphenyl-1H-pyrazol-1-nonanoic acid hydrate

A mixture of methyl 3,4,5-triphenyl-1H-pyrazol-1-nonanoate (3.45 g, 7.4 mmol), 5 N sodium hydroxide solution (4.44 mL, 22 mmol) and methanol (60 mL) was heated at reflux for 1 hour. The solvent was evaporated, the residue diluted with water and 2 N hydrochloric acid solution added until pH =1. A yellow solid was filtered off and recrystallized from dichloromethane/hexane to afford 3,4,5-triphenyl-1H-pyrazol-1-nonanoic acid hydrate (3 g, 89%); m.p. =110°-112° C. MS(CI): m/e =453 (MH+).

IR (KBr) $\nu_{max}$:1715 ($CO_2$ H) cm$^{-1}$.

$1_H$ NMR (DMSO) δ:1.13 (8H, m, CH$_2$), 1.43 (2 H, t, J =6.5 Hz, CH$_2$), 1.71 (2 H, t, J =6 Hz, CH$_2$), 2.12 (2 H, t, J =7 Hz, CH$_2$CO$_2$), 3.99 (2 H, t, J =7 Hz, N-CH$_2$), 7.01–7.59 (15 H, m, aromatic H).

Anal. Calcd. for $C_{30}H_{32}N_2O_2 \cdot 2.01H_2O$:
C, 79.30; H, 7.15; N, 6.17; H$_2$O, 0.40;
Found: C, 79.10; H, 7.18; N, 6.06; H$_2$O, 0.36.

EXAMPLE 16

Methyl 3,4-diphenyl-1H-pyrazol-1-nonanoate and methyl 4,5-diphenyl-1H-pyrazol-1-nonanoate Sodium hydride (945 mg of a 60% dispersion, 23 mmol) was washed three times with hexane, covered with DMF (60 mL) and a mixture of 3,4-diphenyl-1H-pyrazole and 4,5-diphenyl-1H-pyrazole (4 g, 18 mmol) added in one portion. The mixture was stirred at room temperature for 20 minutes before adding methyl 9-bromononoate (5.02 g, 20 mmol) and stirring continued a further 2 hours. The mixture was poured onto water and extracted three times with diethyl ether. The combined extracts were washed with water (3 times), dried over sodium sulfate and concentrated to furnish an oil. Chromatography on a column of silica gel using a mixture of hexane and diethyl ether (2:1) as eluent furnished methyl 3,4-diphenyl-1H-pyrazol-1-nonanoate (4.43 g, 62%) as an oil. MS(CI): m/e =391 (MH+).

IR (film) $\nu_{max}$:1740 (CO$_2$R) cm$^{-1}$.

$1_H$ NMR (CDCl$_3$) δ: 1.20–1.50 (8H, m, CH$_2$), 1.63 (2 H, m, CH$_2$), 1.94 (2 H, m, CH$_2$), 2.29 (2 H, t, J =7.5 Hz, —CH$_2$CO$_2$), 3.64 (3H, s, CO$_2$CH$_3$), 4.14 (2 H, t, J =7 Hz, N-CH$_2$), 7.20–7.40 (8H, m, aromatic H), 7.46 (1 H, s, pyrazole CH), 7.50–7.60 (2 H, m, aromatic H).

Anal. Calcd. for $C_{25}H_{30}N_2O_2$:
C, 76.89; H, 7.74; N, 7.17;
Found: C, 77.15; H, 7.86; N, 7.40.

Further elution of the silica gel column provided a mixed fraction (1.00 g, 14%) followed by methyl 4,5-diphenyl-1H-pyrazol-1-nonanoate (1.00 g, 14%) as an oil. MS(CI): m/e =391 (MH+).

IR (film) $\nu_{max}$:1740 (CO$_2$R) cm$^{-1}$.

$1_H$ NMR (CDCl$_3$) δ: 1.10–1.35 (8H, m, CH$_2$), 1.55 (2 H, quintet, J =7 Hz, CH$_2$), 1.74 (2 H, quintet, J =7 Hz, CH$_2$), 2.25 (2 H, t, J =7.5 Hz, CH$_2$CO$_2$), 3.63 (3H, s, CO$_2$CH$_3$), 3.99 (2 H, t, J =7 Hz, N-CH$_2$), 7.00–7.55 (10H, m, aromatic H), 7.75 (1 H, s, pyrazole CH).

Anal. Calcd. for $C_{25}H_{30}N_2O_2$:
C, 76.89; H, 7.76; N, 7.17;
Found: C, 76.77; H, 7.85; N, 7.21.

EXAMPLE 17

3,4-Diphenyl-1H-pyrazol-1-nonanoic acid hydrate

Hydrolysis of methyl 3,4-diphenyl-1H-pyrazol-1-nonanoate (3 g, 7.7 mmol) by the procedure described in Example 15 afforded 3,4-diphenyl-1H-pyrazol-1-nonanoic acid hydrate (2.23 g, 77%) as a white solid; m.p. =83°–85° C. MS(CI): m/e =377 (MH+).

IR (KBr) $\nu_{max}$:1720 ($CO_2$ H) $cm^{-1}$.

$1_H$ NMR ($CDCl_3$) δ: 1.20–1.50 (8H, m, $CH_2$), 1.61 (2 H, quintet, J =7 Hz, $CH_2$), 1.92 (2H, quintet, J =7 Hz, $CH_2$), 2.31 (2 H, t, J =7.5 Hz, $CH_2CO_2$), 4.15 (2 H, t, J =7 Hz, N-$CH_2$), 7.15–7.30 (8H, m, aromatic H), 7.40 (1 H, s, pyrazole H), 7.40–7.60 (2 H, m, aromatic H).

Anal. Calcd. for $C_{24}H_{28}N_2O_2$:
C, 75.84; H, 7.54; N, 7.38; $H_2O$, 0.95;
Found: C, 75.54; H, 7.47; N, 7.38; $H_2O$, 0.56.

EXAMPLE 18

4,5-Diphenyl-1H-pyrazol-1-nonanoic acid

Hydrolysis of methyl 4,5-diphenyl-1H-pyrazol-1-nonanoate (850 mg, 2 mmol) by the procedure described in Example 15 furnished 4,5-diphenyl-1H-pyrazol-1-nonanoic acid (800 mg, 97%) as an oil after chromatography on a column of silica gel using diethyl ether as eluent. MS(CI): m/e =377 (MH+).

IR (film) $\nu_{max}$: 1720 ($CO_2$ H) $cm^-$ $1_H$ NMR ($CDCl_3$) δ: 1.20–1.40 (8H, m, $CH_2$), 1.59 (2 H, quintet, J =7 Hz, $CH_2$), 1.74 (2 H, quintet, J =7 Hz, $CH_2$), 2.31 (2 H, t, J =7.5 Hz, $CH_2CO_2$), 4.00 (2 H, t, J =7 Hz, N-$CH_2$), 7.00–7.60 (10H, m, aromatic H), 7.79 (1 H, s, pyrazole CH).

Anal. Calcd. for $C_{24}H_{28}N_2O_2$:
C, 76.57; H, 7.50; N, 7.44;
Found: C, 76.62; H, 7.78; N, 7.78.

EXAMPLE 19

1-(6-Bromohexyl)-3,4,5-triphenyl-1H-pyrazol

Bromine (3.44 g, 21 mmol) was added dropwise to a solution of triphenylphosphine (5.65 g, 21 mmol) in DMF (20 mL) maintained under an atmosphere of nitrogen. After 30 minutes, a solution of 3,4,5-triphenyl-1H-pyrazol-1-hexanol (7.11 g, 18 mmol) in DMF (25 mL) was added in one portion. The mixture was stirred at room temperature for 20 minutes before being poured onto diethyl ether (500 mL) and washed with water (twice) and saturated sodium chloride solution (twice). The ethereal layer was dried over magnesium sulphate and the solvent evaporated to leave an oil. Chromatography on a column of silica gel using a mixture of hexane, ethyl acetate and triethylamine (9:1:01) afforded 1-(6-bromohexyl)-3,4,5-triphenyl-1H-pyrazole (6.98 g 84%) as a yellow oil. MS(CI): m/e =458 (MH+).

$1_H$ NMR ($CDCl_3$) δ:1.20 to 1.40 (4 H, m $CH_2$), 1.70 to 1.95 (4 H, m, $CH_2$), 3.33 (2 H, t, J =7 Hz, $CH_2Br$), 4.08 (2 H, t, J =7 Hz, N-$CH_2$), and 7.00 to 7.60 (15 H, m, aryl H).

EXAMPLE 20

Methyl [[6-(3,4,5-triphenyl-1H-pyrazol-1-yl)hexyl]thio]acetate

A mixture of 1-(6-bromohexyl)-3,4,5-triphenyl-1H-pyrazole (6.53 g, 14 mmol), methyl mercaptoacetate (1.66 g, 15 mmol), potassium carbonate (2.26 g, 16.5 mmol), potassium iodide (catalytic amount) and acetonitrile (150 mL) was heated at reflux for 4 hours. The mixture was cooled, filtered and concentrated in vacuo to give an oil. Chromatography on a column of silica gel using a mixture of hexane and ethyl acetate (4:1) as eluent furnished methyl [[6-(3,4,5-triphenyl-1H-pyrazol-1-yl)hexyl]thio]acetate (6.47 g, 91%) as an oil.

IR (film) $\nu_{max}$:1740 (C=O) $cm^{-1}$.

$1_H$ NMR ($CDCl_3$) δ:1.28 (4 H, m, $CH_2$), 1.53 (2 H, quintet, J =7.5 Hz, $CH_2$), 1.84 (2 H, quintet, J =7.5 Hz, $CH_2$), 2.55 (2 H, t, J =7 Hz, $CH_2$—S) 3.17 (2 H, s, S—$CH_2CO_2CH_3$), 3.70 (3H, s, $CO_2CH_3$), 4.06 (2 H, t, J =7.5 Hz, N-$CH_2$), 6.99 to 7.50 (15 H, m, aryl H). m/e 485 (MH+).

Anal. Calcd. for $C_{30}H_{32}N_2O_2S$:
C, 74.35; H, 6.66; N, 5.79;
Found: C, 74.06; H, 6.82; N, 6.02.

EXAMPLE 21

[[6-(3,4,5-Triphenyl-1H-pyrazol-1-yl)hexyl]thio]acetic acid

A mixture of methyl [[6-(3,4,5-triphenyl-1H-pyrazol-1-yl)hexyl]thio]acetate (1.01 g, 2 mmol), 3 N sodium hydroxide solution (2.1 mL, 6 mmol) and methanol (125 mL) was heated at reflux for 20 minutes. The solvent was removed and the residue treated with 1N hydrochloric acid solution. Extraction with dichloromethane (three times) followed by drying of the organic phase over sodium sulfate and concentration in vacuo afforded an oil that crystallized on standing to give [[6-(3,4,5-triphenyl-1H-pyrazol-1-yl) hexyl]thio]acetic acid (0.94 g, 96%); m.p. =92°–97° C. MS(CI): m/e =471 (MH+).

IR (film) $\nu_{max}$:1705 ($CO_2$ H) $cm^{-1}$.

$1_H$ NMR ($CDCl_3$) δ: 1.20 to 1.50 (4 H, m, $CH_2$), 1.59 (2 H, quintet, J =7 Hz, $CH_2$), 1.83 (2 H, quintet, J =7 Hz, $CH_2$) 2.61 (2 H, t, J =7 Hz, $CH_2$—S), 3.18 (2 H, s, $CH_2CO_2H$), 4.10 (2 H, t, J =7.5 Hz, N-$CH_2$), 6.95 to 7.50 (15 H, m, aryl H), 9.72 (1 H, bs, $CO_2$ H).

Anal. Calcd. for $C_{29}H_{30}N_2O_2S$:
C, 74.02; H; 6.43; N, 5.96;
Found: C, 74.33; H, 6.47; N, 5.93.

EXAMPLE 22

Methyl [6-(3,4,5-triphenyl-1H-pyrazol-1-yl)hexyl]sulfonyl]acetate

Oxone (potassium monopersulfate compound)(3.80 g, 6 mmol) suspended in water (20 mL) was added slowly to a stirred solution of methyl [[6-(3,4,5-triphenyl-1H-pyrazol-1-yl)hexyl]thio] acetate (1.00 g, 2 mmol) in methanol (20 mL) maintained at 0° C. The reaction mixture was allowed to warm to room temperature and stirred for 5.5 hours before being poured onto water. The mixture was extracted with diethyl ether, the ethereal layer washed twice with saturated sodium chloride solution, dried over magnesium sulfate and concentrated in vacuo. Crystallization of the residue from a mixture of hexane and dichloromethane (25:1) afforded methyl [[6-(3,4,5-triphenyl 1H-pyrazol-1-yl)hexyl]sulfonyl]acetate (1.17 g, 91%); m.p. =92.5°–94.5° C. MS(CI): m/e =517 (MH+).

IR (KBr) $\nu_{max}$:1760 ($CO_2CH_3$), and 1315 ($SO_2$) $cm^{-1}$.

$1_H$ NMR ($CDCl_3$) δ:1.20 to 1.40 (4 H, m, $CH_2$), 1.65 to 1.90 (4 H, m, $CH_2$), 3.16 (2 H, t, J =7.5 Hz, $CH_2SO_2$), 3.78 (3H, s, $CO_2CH_3$), 3.90 (2 H, s, $SO_2CH_2CO_2CH_3$), 4.08 (2 H, t, J =7 Hz, N-CH$_2$) and 6.90 to 7.50 (15 H, m, aryl H).

Anal Calcd. for C$_{30}$H$_{32}$N$_2$O$_4$S:
C, 69.75; H, 6.25; N, 5.43;
Found: C, 70.12; H, 6.40; N, 5.29.

EXAMPLE 23

[[6-(3,4,5-Triphenyl-1H-pyrazol-1-yl)hexyl]sulfonyl]acetic acid

A mixture of methyl [[6-(3,4,5-triphenyl-1H-pyrazol-1-yl)hexyl]sulfonyl]acetate (0.94 g, 2 mmol), 3 N sodium hydroxide solution (2.43 mL, 7 mmol) and methanol (100 mL) was heated at reflux. After 20 minutes, the methanol was removed in vacu. the residue acidified with 1N HCl and extracted with dichloromethane. The organic phase was washed with saturated sodium chloride solution, dried over sodium sulfate and concentrated to give a foam. Recrystallization from a mixture of dichloromethane and hexane (1:3) afford [[6-(3,4,5-triphenyl-1H-pyrazol-1-yl) hexyl]sulfonyl]acetic acid (0.80 g, 88%); m.p.=153.5°–155° C. MS(CI): m/e =459 (MH$^+$).

IR (KBr) $v_{max}$:1733 (CO$_2$ H) and 1320 (SO$_2$) cm$^{-1}$.

$1_H$ NMR (CDCl$_3$) δ: 1.20 to 1.40 (4 H, m, CH$_2$), 1.65 to 1.85 (4 H, m, CH$_2$), 3.14 (2 H, t, J =7 Hz, CH$_2$SO$_2$), 3.25 (2 H, m, CH$_2$CO$_2$ H), 4.02 (2 H, t, J =7.5 Hz, N-CH$_2$), 6.90 to 7.40 (15 H, m, aryl H).

Anal. Calcd. for C$_{29}$H$_{30}$N$_2$O$_4$S:
C, 69.30; H, 6.02; N, 5.58;
Found: C, 69.07; H, 6.17; N, 5.74.

EXAMPLE 24

Methyl [[6-(3,4,5-triphenyl-1H-pyrazol-1-yl)hexyl]sulfinyl] acetate hydrate

Oxone (potassium monopersulfate compound) (3.30 g, 5 mmol) was added in one portion to a stirred mixture of methyl [[6-(3,4,5-triphenyl-1H-pyrazol-1-yl)hexyl]thio] acetate (2.08 g, 4.3 mmol), methanol (100 mL) and water (50 mL) maintained at −10° C. The mixture was allowed to warm slowly to 0° C. and stirred for 45 minutes before being diluted with water and chloroform. The organic phase was separated and the aqueous layer extracted with CHCl$_3$. The combined organic layers were washed with saturated sodium chloride solution, dried over sodium sulfate and concentrated in vacuo to give an oil. Chromatography on a column of silica gel using a mixture of ethyl acetate and hexane (7:3) as eluent furnished methyl [[6-(3,4,5-triphenyl-1H-pyrazol-1- yl)hexyl]sulfinyl]acetate hydrate (1.84 g, 85%) that slowly crystallized; m.p. =70.5°–71.5° C. MS(CI): m/e=501 (MH$^+$).

IR (film) $v_{max}$:1740 (CO$_2$CH$_3$), 1050 (S=O) cm$^{-1}$.

$1_H$ NMR (CDCl$_3$) δ: 1.25 to 1.45 (4 H, m, CH$_2$), 1.65 to 1.90 (4 H, m, CH$_2$), 2.75 (2 H, two triplets, J =7 Hz, CH$_2$SO), 3.62 (2 H, s, CH$_2$CO$_2$CH$_3$), 3.76 (3H, s, CO$_2$CH$_3$) 4.08 (2 H, t, J =7.5 Hz, N-CH$_2$), 6.90 to 7.50 (15 H, m, aryl H).

Anal. Calcd. for C$_{30}$H$_{32}$N$_2$O$_3$S·0.1 H$_2$O:
C, 71.72; H, 6.46; N, 5.58; H$_2$O, 0.36;
Found: C, 71.40; H, 6.58; N, 5.79; H$_2$O, 0.37.

EXAMPLE 25

[[6-(3,4,5-Triphenyl-1H-pyrazol-1-yl)hexyl]sulfinyl]acetic acid hydrate

A mixture of methyl [[6-(3,4,5-triphenyl-1H-pyrazol-1-yl)hexyl]sulfinyl]acetate (1.06 g, 2.1 mmol), 3 N sodium hydroxide solution (2.1 mL, 6.3 mmol) and methanol (50 mL) was heated at reflux for 10 minutes. The methanol was evaporated, the residue acidified to pH=5 with 1N HCl and extracted with dichloromethane (3x). The combined extracts were washed with saturated sodium chloride solution, dried over sodium sulfate and concentrated to afford [[6-(3,4,5-triphenyl-1H-pyrazol-1-yl)hexyl]sulfinyl]acetic acid hydrate (0.98 g, 95%) as a white foam; m.p. =132.5°–134.5° C. MS(CI): m/e =443 (MH$^+$—CO$_2$).

IR (KBR) $v_{max}$:1720 (CO$_2$ H), 1030 (S=O) cm$^{-1}$.

$1_H$ NMR (CDCl$_3$) δ: 1.25 to 1.40 (4 H, m, CH$_2$), 1.65 to 1.85 (4 H, m, CH$_2$), 2.75 to 2.95 (2 H, m, CH$_2$SO), 3.68 (2 H, s, CH$_2$CO$_2$ H), 4.10 (2 H, t, J =7.5 Hz, N-CH$_2$), 6.75 to 7.50 (15 H, m, aryl H), 9.82 (1 H, bs, CO$_2$ H).

Anal. Calcd. for C$_{20}$H$_{30}$N$_2$O$_3$S·0.1 H$_2$O:
C, 71.32; H, 6.24; N, 5.74; H$_2$O, 0.37;
Found: C, 71.07; H, 6.26; N, 5.76; H$_2$O, 0.23.

EXAMPLE 26

Methyl [[5-(3,4,5-triphenyl-1H-pyrazol-1-yl)pentyl]thio] acetate

When the general procedure of Example 20 was repeated with 1-(5-bromopentyl)-3,4,5-triphenyl-1H-pyrazole, the title compound was thereby produced in 100% yield as an oil. MS(CI): m/e =471 (MH$^+$).

IR (film) $v_{max}$:1740 (CO$_2$CH$_3$) cm$^{-1}$.

$1_H$ NMR (CDCl$_3$) 1.37 (2 H, quintet, J =6 Hz, CH$_2$), 1.54 (2 H, quintet, J =7 Hz, CH$_2$), 1.87 (2 H, quintet, J =7 Hz, CH$_2$), 2.56 (2 H, t, J =7 Hz, CH$_2$—S), 3.16 (2 H, s, CH$_2$CO$_2$CH$_3$), 3,70 (3H, s, CO$_2$CH$_3$), 4.08 (2 H, t, J =7.5 Hz, N-CH$_2$), 7.00 to 7.50 (15 H, m, aryl H).

Anal. Calcd. for C$_{29}$H$_{30}$N$_2$O$_2$S:
C, 74.02; H, 6.43; N, 5.90;
Found: C, 73.75; H, 6.70; N, 5.87.

EXAMPLE 27

[[5-(3,4,5-Triphenyl-1H-pyrazol-1-yl)pentyl]thio]acetic acid

When the compound of Example 26 was treated by the general procedure described in Example 21, the title compound was thereby produced in 96% yield as a white solid; m.p. =140°–142° C. MS(CI): m/e =457 (MH$^+$).

IR (KBr) $v_{max}$:1710 (CO$_2$ H)cm$^{-1}$.

$1_H$ NMR (CDCl$_3$) δ: 1.35 (2 H, quintet, J =7 Hz, CH$_2$), 1.52 (2 H, quintet, J =7 Hz, CH$_2$), 1.84 (2 H, t, J =7 Hz, CH$_2$), 2.59 (2 H, t, J =7 Hz, S—CH$_2$), 3.17 (2 H, s, SCH$_2$—CO$_2$ H), 4.10 (2 H, t, J =7 Hz, N—CH$_2$), 6.75 to 7.50 (15 H, m, aryl H), 10.24 (1 H, bs, CO$_2$ H).

Anal. Calcd. for C$_{28}$H$_{28}$N$_2$OS:
C, 73.66; H, 6.19; N, 6.14;
Found: C, 73.83; H, 6.33; N, 6.11.

EXAMPLE 28

Methyl [5-(3,4,5-triphenyl-1H-pyrazol-1-yl)pentyl]sulfonyl]acetate

When the compound of Example 26 was oxidized by the general method described in Example 22, there was thereby produced the title compound as a white solid in 85% yield; m.p. =101.5°–102.5° C. MS(CI): m/e =503 (MH$^+$).

IR (KBr) $v_{max}$:1747 (CO$_2$CH$_3$), 1315 (SO$_2$) cm$^{-1}$.

$^1H$ NMR (CDCl$_3$): δ1.43 (2 H, quintet, J =7 Hz, CH$_2$), to 1.95 (4 H, m, CH$_2$), 3.18 (2 H, t, J =7 Hz, CH$_2$SO$_2$), 3.78 (3H, s, CO$_2$CH$_3$), 3.90 (2 H, s, CH$_2$CO$_2$CH$_3$), 4.10 (2 H, t, J =7 Hz, N—CH$_2$), 6.95 to 7.50 (15 H, m, aryl H).

Anal. Calcd. for C$_{29}$H$_{30}$N$_2$O$_4$S:
C, 69.30; H, 6.02; N, 5.58;
Found: C, 69.60; H, 6.20; N, 5.86.

EXAMPLE 29

[[54-(3,4,5-Triphenyl-1H-pyrazol-1-yl)pentyl]sulfonyl]acetic acid

When the compound of Example 28 was hydrolyzed by the procedure described in Example 23, the title compound was thereby produced as a white solid in 85% yield; m.p. =200°-200.5°. MS(CI): m/e =489 (MH+), 446 (MH+—CO$_2$).

IR (KBr) ν$_{max}$:1720 (CO$_2$H), 1310 (SO$_2$) cm$^{-1}$.

$^1H$ NMR (CDCl$_3$/ DMSO) δ: 1.17 (2 H, quintet J =7 Hz, CH$_2$), 1.45 to 1.70 (4 H, m, CH$_2$), 2.97 (2 H, 6, J =7 Hz, CH$_2$SO$_2$), 3.66 (2 H, s, CH$_2$CO$_2$H), 3.83 (2 H, t, J =7 Hz, N—CH$_2$), 6.70 to 7.30 (15 H, m, aryl H).

Anal. Calcd. for C$_{28}$H$_{28}$N$_2$O$_4$S:
C, 68.84; H, 5.78; N, 5.74;
Found: C, 68.84; H, 5.76; N, 5.47.

EXAMPLE 30

Methyl [[5-(3,4,5-triphenyl-1H-pyrazol-1-yl)pentyl]-sulfinyl]acetate

When the compound of Example 26 was oxidized following the procedure described in Example 24, the title compound was thereby produced in 77% yield as a white solid; m.p. = 108.5°-109.0° C. MS(CI): m/e =487 (MH+).

IR (KBr) ν$_{max}$:1748 (CO$_2$CH$_3$), 1040 (S=O)cm$^{-1}$.

$^1H$ NMR (CDCl$_3$) 1.45 (2 H, m, CH$_2$), 1.73 (2 H, m, CH$_2$), 1.89 (2 H, t, J =7 Hz, CH$_2$), 2.78 (2 H, t, J =7 Hz, CH$_2$·SO), 3.62 (2 H, s, CH$_2$·CO$_2$CH$_3$), 3.75 (3H, s, CO$_2$CH$_3$), 4.09 (2 H, t, J =7 Hz, N—CH$_2$), 6.95 to 7.50 (15 H, m, aryl H).

Anal. Calcd. for C$_{29}$H$_{30}$N$_2$O$_3$S:
C, 71.58; H, 6.22; N, 5.76;
Found: C, 71.58; H, 6.28; N, 5.68.

EXAMPLE 31

[[5-(3,4,5-Triphenyl-1H-pyrazol-1-yl)pentyl]sulfinyl]acetic acid

When the compound of Example 30 was hydrolyzed following the procedure of Example 25, the title compound was thereby produced in 96% yield as a white solid; m.p. =129°-130.5° C. MS(CI): m/e =429 (MH+—CO$_2$).

IR (KBr) ν$_{max}$:1720 (CO$_2$H), 1020 (S=O) cm$^{-1}$.

$^1H$ NMR (CDCl$_3$) 1.30 to 1.50 (2 H, m, CH$_2$), 1.71 (2 H, quintet, J =7 Hz, CH$_2$), 1.85 (2 H, quintet, J =7 Hz, CH$_2$), 2.70 to 2.90 (2 H, m, CH$_2$SO), 3.63 (2 H, AB quartet, J$_{AB}$ =14 Hz, SO·CH$_2$CO$_2$H), 4.10 (2 H, q, J =7 Hz, N—CH$_2$), 6.85 to 7.50 (15 H, m, aryl H).

Anal. Calcd. for C$_{28}$H$_{28}$N$_2$O$_3$S:
C, 71.17; H, 5.98; N, 5.93;
Found: C, 71.19; H, 6.00; N, 6.25.

EXAMPLE 32

(Z) and (E)-Methyl-11-(3.4.5-triphenyl-1H-pyrazol-1-yl)-5-undecenoate

Esterification of the compound of Example 12 by a procedure analogous to Example 11 produced 0.91 g of the title compound in 88% yield. MS(CI): m/e =493 (MH+).

IR (film) ν$_{max}$:1740 (CO$_2$CH$_3$) cm$^{-1}$.

$^1H$ NMR (CDCl$_3$) δ: 1.18 to 1.35 (4 H, m, CH$_2$), 1.65 (2 H, quintet, J=7 Hz, CH$_2$), 1.78 to 2.20 (6H, m, CH$_2$), 2.28 (2 H, m, CH$_2$) 3.62 and 3.63 (3H, singlets, CO$_2$CH$_3$), 4.06 (2 H, t, J=7 Hz, N—CH$_2$), 5.20 to 5.40 (2 H, m, vinylic H), 6.90 to 7.60 (15 H, m, aromatic H).

Anal. Calcd. for C$_{33}$H$_{36}$N$_2$O$_2$:
C, 80.46; H, 7.37; N, 5.69;
Found: C, 80.42; H, 7.47; N, 5.55.

EXAMPLE 33

Methyl 3,4,5-triphenyl-1H-pyrazol-1-undecanoate hydrate

Esterification of the compound of Example 13 by a procedure analogous to Example 11 produced 1.01 g of the title compound in 85% yield. MS(CI): m/e =495 (MH+).

IR (film) ν$_{max}$:1745 (CO$_2$CH$_3$) cm$^{-1}$.

$^1H$ NMR (CDCl$_3$) δ: 1.10 to 1.30 (16H, m, CH$_2$), 1.59 (2 H, quintet, J=7 Hz, CH$_2$), 1.84 (2 H, quintet, J=7 Hz, CH$_2$), 2.28 (2 H, t, J=7 Hz, CH$_2$CO$_2$CH$_3$), 3.64 (3H, s, CO$_2$CH$_3$), 4.06 (2 H, t, J=7 Hz, N—CH$_2$) 6.90 to 7.00 (15 H, m, aromatic H).

Anal Calcd. for C$_{33}$H$_{38}$N$_2$O$_2$·0.4 H$_2$O:
C, 78.98; H, 7.80; N, 5.59; H$_2$O, 1.44;
Found: C, 79.07; H, 7.85; N, 5.95; H$_2$O, 2.88.

EXAMPLE 34

3,4,5-Triphenyl-1H-pyrazole-1-undecene

A mixture of sodium hydride (50% dispersion, 0.2 g, 4 mmol, prewashed with hexane) and 3,3,5-triphenyl-3H-pyrazole (1.00 g, 3.4 mmol) in DMF (15 mL) was heated to 110° C. under an atmosphere of nitrogen. After 50 minutes, the solution was cooled to room temperature and 11-bromoundecene (0.81 g, 3.7 mmol) added. The mixture was stirred at room temperature overnight, poured onto water and extracted with diethyl ether. The combined extracts were washed with water (3 x), and saturated sodium chloride solution, dried and the solvent removed. The residue was chromatographed on a column of silica gel using a mixture of hexane and ethyl acetate (9:1) containing 1% triethyl amine to give 3,4,5-triphenyl-1H-pyrazole -1-undecene (1.51 g, 100%) as an oil. MS(CI): m/e =448 (MH+).

IR (film) ν$_{max}$:1640 (C=C) cm$^{-1}$.

$^1H$ NMR (CDCl$_3$) δ: 1.15 to 1.55 (12 H, m, CH$_2$), 1.86 (2 H, quintet, J=7 Hz, CH$_2$), 2.03 (2 H, q, J=7 Hz, allylic CH$_2$), 4.08 (2 H, t, J=7 Hz, N—CH$_2$), 4.90 to 5.30 (2 H, m, vinylic H), 5.70 to 5.90 (1 H, m, vinylic H), 6.95 to 7.60 (15 H, m, aromatic H).

EXAMPLE 35

3,4,5-Triphenyl-1H-pryazole-1-decanal

Oxone was bubbled through a solution of 3,4,5-triphenyl-1H-pyrazole-1-undecene (6.78 g, 15 mmol) in dichloromethane (175 mL) and methanol (0.73 g, 22 mmol) maintained at −78° C. for 1.5 hours. The ozone supply was removed, dimethylsulfide (30 mL) added and the mixture allowed to warm to room temperature over 2 hours. The solution was dried over sodium sulfate, concentrated in vacuo and the residue chromatographed on a column of silica gel. Elution with a mixture of hexane and ethyl acetate (9:1) gave 3,4,5-triphenyl-lH-pyrazole-1-decanal (2.93 g, 43%) as an oil. MS(CI): m/e =451 (MH+).

IR (film) $v_{max}$:1730 (CHO) cm$^{-1}$.

$1_H$ NMR (CDCl$_3$) δ: 1.10 to 1.40 (10 H, m, CH$_2$), 1.57 (2 H, quintet, J=7 Hz, CH$_2$), 1.82 (2 H, quintet, J=7 Hz, CH$_2$), 2.38 (2 H, dt, J=7 Hz, Jl=2 Hz, CH$_2$·CHO), 4.05 (2 H, t, J=7 Hz, N—CH$_2$), 6.95 to 7.50 (15 H, m, aromatic H), 9.72 (1 H, d, J=2 Hz, CHO).

EXAMPLE 36

3,4,5-triphenyl-lH-pyrazole-1-decanoic acid hydrate

To a solution of 3,4,5-triphenyl-lH-pyrazole-1-decanal (2.42 g, 5.4 mmol) in acetone (47 mL maintained at 0° C. was added dropwise 1.75 mL (7 mmol) of 8 N Jones reagent. The ice water was removed and the mixture stirred for 48 minutes before being diluted with acetone, filtered through diatomaceous earth and concentrated. The residual oil was chromatographed on a column of silica gel using a mixture of hexane and ethyl acetate (13:7) as eluent to afford 3,4,5-triphenyl-lH-pyrazole-1-decanoic acid hydrate (2.46 g, 81%) as an oil. MS(CI): m/e =467 (MH+).

IR (film) $v_{max}$:1720 (CO$_2$H) cm$^{-1}$.

$1_H$ NMR (CDCl$_3$) δ:1.05 to 1.25 (10H, bs, CH$_2$), 1.60 (2 H, quintet, J=7 Hz, CH$_2$), 1.85 (2 H, quintet, J=7 Hz, CH$_2$), 2.32 (2 H, t, J=7 Hz, CH$_2$·CO$_2$H), 4.11 (2 H, t, J=7 Hz, N—CH$_2$), 6.95 to 7.60 (15 H, m, aromatic H), 10.11 (1H, bs, CO$_2$H).

Anal. Calcd. for $C_{31}H_{34}N_2O_2$·0.2 H$_2$O:
C, 79.19; H, 7.38; N, 5.96; H$_2$O, 0.77;
Found: C, 79.16; H, 7.39; N, 5.86; H$_2$O, 0.79.

EXAMPLE 37

Methyl 3,4,5-triphenyl-lH-pyrazole-1-decanoate

The title compound (1.03 g, 62%) was prepared from 3,4,5-triphenyl-lH-pyrazole-1-decanoic acid (1.60 g) by esterification in methanol using a catalytic amount of conc. sulfuric acid. MS(CI): m/e =481 (MH+).

IR (film) $v_{max}$:1740 (CO$_2$CH$_3$) cm$^{-1}$.

$1_H$ NMR (CDCl) δ: 1.21 (10 H, bs, CH$_2$), 1.58 (2 H, quintet, J=7 Hz, CH$_2$), 1.84 (2 H, quintet, J=7 Hz, CH$_2$), 2.27 (2 H, t, J=7 Hz, CH$_2$·CO$_2$CH$_3$), 3.64 (3H, s, CO$_2$CH$_3$), 4.07 (2 H, t, J=7 Hz, N—CH$_2$), 6.90 to 7.50 (15 H, m, aromatic H).

Anal. Calcd. for $C_{32}H_{36}N_2O_2$:
C, 79.97; H, 7.55; N, 5.83;
Found: C, 79.95; H, 7.62; N, 5.96.

EXAMPLE 38

3,4,5-Triphenyl-lH-pyrazole-1-hexanoic acid

Hydrolysis of 1.5 g of ethyl 3,4,5-triphenyl-lH-pyrazole-1-hexanoate with aqueous ethanolic sodium hydroxide solution gave 1.3 g (92%) of the product. Recrystallization from CH$_2$Cl$_2$-hexane produced the title compound; m.p. =140°-142° C. MS(CI): m/e =411 (MH+).

IR (KBr) $v_{max}$:1715 (CO$_2$H) cm$^{-1}$.

$1_H$ NMR (DMSO-d$^6$) δ: 1.84 (2 H, quintet, J=7 Hz, CH$_2$), 1.38 (2 H, quintet, J=7 Hz, CH$_2$), 1.72 (2 H, quintet, J=7 Hz, CH$_2$), 2.11 (2 H, t, J=7 Hz, CH$_2$), 3.98 (2 H, t, J=7 Hz, N—CH$_2$), 6.95 to 7.50 (15 H, m, aromatic H), 11.97 (1H, s, CO$_2$ H). MS(CI: m/e =411 (MH+).

Anal. Calcd. for $C_{27}H_{26}N_2O_2$:
C, 79.00; H, 6.38; N, 6.82;
Found: C, 78.95; H, 6.39; N, 6.93.

EXAMPLE 39

3,4,5-Triphenyl-lH-pyrazole-1-nonanenitrile hemihydrate

A stirred mixture of potassium cyanide (0.4 g, 6.1 mmol), 1-(8-bromooctyl)-3,4,5-triphenyl-lH-pyrazole (2.70 g, 5.5 mmol) and DMF (30 mL was heated at 70° C. under an atmosphere of nitrogen. After 58 hours, the reaction mixture was diluted with water and extracted with dichloromethane (3 x). The combined extracts were washed with water, saturated sodium chloride solution, dried over sodium sulfate and concentrated to leave an oil. Chromatography on a column of silica gel using a mixture ethyl acetate, hexane and triethylamine (20:79:1) as eluent gave 3,4,5-triphenyl-lH-pyrazole-1-nonanenitrile hemihydrate (1.27 g, 52%) as a beige solid. An analytical sample, recrystallized from a mixture of dichloromethane and hexane, had m.p.=79.5°-80.5° C. MS(CI): m/e =434 (MH+).

IR (KBr) $v_{max}$:2230 (CN) cm$^{-1}$.

$1_H$ NMR (CDCl$_3$) δ: 1.24 (8H, bs, CH$_2$), 1.60 (2 H, quintet, J=7 Hz, CH$_2$·CN), 4.07 (2 H, t, J=7 Hz, N—CH$_2$), 6.95 to 7.60 (15 H, m, aromatic H).

Anal. Calcd. for $C_{30}H_{31}N_3$·0.5 H$_2$O:
C, 81.42; H, 7.29; N, 9.50; H$_2$O, 2.04;
Found: C, 81.38; H, 7.18; N, 9.35; H$_2$O, 0.73.

EXAMPLE 40

5-[8-(3,4,5-Triphenyl-lH-pyrazol-1-yl)octyl]-2 H-tetrazole

A mixture of 3,4,5-triphenyl-lH-pyrazole-1-nonanenitrile (1.25 g, 2.9 mmol) and tri-n-butyltin azide (1.15 g, 3.5 mmol) was heated with stirring at 140° C. under an atmosphere of nitrogen. After 2.5 hours, the mixture was cooled to room temperature, diluted with ethyl acetate and washed with 0.5 N HCl (3 x) and saturated sodium chloride solution before being dried and concentrated in vacuo. The residual oil was chromatographed on a column of silica gel using first a mixture of ethyl acetate and hexane (1:1) and subsequently methanol/chloroform (1:9) as eluent. The recovered oil was dissolved in CH$_2$Cl$_2$ and stirred with a concentrated aqueous solution of potassium floride. After 24 hours, the layers were separated and the aqueous layer extracted with dichloromethane. The organic extracts were dried over sodium sulfate and concentrated in vacuo to give an oil that solidified. Recrystallization from a mixture of hexane and dichloromethane (2:1) afforded the title compound (1.00 g, 73%); m.p.=158°-160° C. MS(CI): m/e =477 (MH+).

IR (KBr) $v_{max}$:2970, 2930 (CH$_2$) cm$^{-1}$.

$1_H$ NMR (CDCl$_3$) δ: 1.14 (8H, m, CH$_2$), 1.60 (2 H, t, J=7 Hz, CH$_2$), 1.79 (2 H, t, J=7 Hz, CH$_2$), 2.74 (2 H, t, J=7 Hz, CH$_2$-tetrazole), 4.10 (2 H, t, J=7 Hz, N—CH$_2$), 6.90 to 7.50 (15 H, m, aromatic H).

Anal. Calcd. for $C_{30}H_{32}N_6$:
C, 75.61; H, 6.77; N, 17.64;
Found: C, 75.25; H, 6.82; N, 17.55.

EXAMPLE 41

3,4-Diphenyl-lH-pyrazole

A mixture of deoxybenzoin (50 g, 0.255 mole) and N,N-dimethylformamide dimethyl acetal (37.9 g, 42.5 ml, 0.32 mole) was stirred at 120° C. under an atmosphere of nitrogen. After 30 minutes the heating source was removed and hydrazine (24 g, 24 ml, 0.75 mole) added dropwise to the hot mixture. After completing the addition, the mixture was poured onto water (600 ml) and a solid filtered off and air dried to afford 3,4-diphenyl-1H-pyrazole (52.18 g, 92%) which was used without further purification. An analytical sample was prepared by recrystallization from ethanol; m.p.=150°-152° C. (lit. m.p. =154°-155° C.).

Anal. Calcd. for $C_{15}H_{12}N_2$:
C, 81.79; H, 5.49; N, 12.72;
C, 81.55; H, 5.57; N, 12.72.

EXAMPLE 42

Methyl 3,4-diphenyl-1H-pyrazole-1-octanoate and methyl 4,5-diphenyl-1H-pyrazole-1-octanoate Sodium hydride (1.57 g of 50% dispersion, 32 mmol) was washed twice with hexanes, covered with DMF (100 mL), and a mixture of 3,4-diphenyl-1H-pyrazole and 4,5-diphenyl-1H-pyrazole (6.00 g, 27 mmol) was added. After gas evolution had ceased, the mixture was stirred for 10 minutes before adding methyl 8-bromooctanoate (7.10 g, 30 mmol). The mixture was stirred at room temperature for 40 minutes, diluted with water, and extracted with diethyl ether (3 times). The combined extracts were washed with water (3 times), dried over sodium sulfate, and concentrated in vacuo to leave an oil. Repeated chromatography on a column of silica gel using a mixture of hexanes and diethyl ether (2:1) as eluant provided methyl 3,4-diphenyl-1H-pyrazole-1-octanoate (6.11 g, 59%) as an oil. MS(CI): m/e =377 (MH+).

IR (film) $\nu_{max}$:1740 ($CO_2R$) cm$^{-1}$.

$1_H$ NMR ($CDCl_3$) δ: 1.35 (6H, bs, $CH_2$), 1.61 (2 H, quintet, J =7 Hz, $CH_2$), 1.92 (2 H, quintet, J =7 Hz, $CH_2$), 2.29 (2 H, t, J =7 Hz, $CH_2 \cdot CO_2Me$), 3.64 (3H, s, $CO_2CH_3$), 4.14 (2 H, t, J =7 Hz, N—$CH_2$), 7.10 to 7.30 (8H, m, aryl H), 7.46 (1 H, s, pyrazole H) and 7.40 to 7.50 (2 H, m, aryl H).

Anal. Calcd. for $C_{24}H_{28}N_2O_2$:
C, 76.56; H, 7.50; N, 7.44;
Found: C, 76.54; H, 7.85; N, 7.30.

Further elution of the silica gel column provided a mixed fraction (1.34 g, 13%) followed by methyl 4,5-diphenyl-1H-pyrazole-1-octanoate (1.28 g, 12%) as an oil. MS(CI): m/e =377 (MH+).

IR (film) $\nu_{max}$:1740 ($CO_2R$) cm$^{-1}$.

$1_H$ NMR ($CDCl_3$) δ: 1.19 (6H, bs, $CH_2$), 1.53 (2 H, quintet, J =7 Hz, $CH_2$), 1.75 (2 H, quintet, J =7 Hz, $CH_2$), 2.24 (2 H, t, J =7 Hz, $CH_2 \cdot CO_2Me$), 3.63 (3H, s, $CO_2CH_3$), 3.97 (2 H, t, J =7 Hz, N—$CH_2$), 7.00 to 7.50 (10 H, m, aryl H) and 7.74 (1 H, s, pyrazole H).

Anal. Calcd. for $C_{24}H_{28}N_2O_2$:
C, 76.56; H, 7.50; N, 7.44;
Found: C, 76.62; H, 7.74; N, 7.20.

EXAMPLE 43

3,4-Diphenyl-1H-pyrazole-1-octanoic acid

A mixture of methyl 3,4-diphenyl-1H-pyrazole 1-octanoate (3.40 g, 9 mmol), lithium hydroxide hydrate (1.13 g, 27 mmol), methanol (60 mL), and water (10 mL) was heated at reflux on a steam bath. After 15 minutes, the solution was concentrated in vacuo, diluted with water and 2 N HCl solution until pH =1. The mixture was extracted with methylene chloride, the combined extracts dried, and the solvent evaporated to leave an oil. Dissolution in diethyl ether followed by the addition of hexanes provided 3,4-diphenyl-1H-pyrazole-1-octanoic acid (2.80 g, 86%); m.p. =108°-110° C. MS(CI): m/e =363 (MH+).

IR (KBr) $\nu_{max}$:1710 ($CO_2$ H) cm$^{-1}$.

$1_H$ NMR ($CDCl_3$) δ: 1.35 (6 H, bs, $CH_2$), 1.62 (2 H, quintet, J =7 Hz, $CH_2$), 1.93 (2 H, quintet, J =7 Hz, $CH_2$), 2.32 (2 H, t, J =7 Hz, $CH_2CO_2$ H), 4.15 (2 H, t, J =7 Hz, N—$CH_2$), 7.10 to 7.35 (8H, m, aryl H), 7.46 (1H, s, pyrazole H) and 7.40 to 7.50 (2 H, m, aryl H).

Anal. Calcd. for $C_{23}H_{26}N_2O_2 \cdot 0.1\ H_2O$:
C, 75.84; H, 7.26; N, 7.70; $H_2O$, 0.5;
Found: C, 76.19; H, 7.64; N, 7.75; $H_2O$, 0.44.

EXAMPLE 44

4,5-Diphenyl-1H-pyrazole-1-octanoic acid

Hydrolysis of methyl 4,5-diphenyl-1H-pyrazole-1-octanoate (0.42 g, 1.2 mmol) using lithium hydroxide monohydrate (0.14 g, 3.3 mmol) in methanol (10 mL) and water 2 mL) as described for the isomer in Example 43 provided 4,5-diphenyl-1H-pyrazole-1-octanoic acid (0.25 g, 61%); m.p. =88°-90° C. MS(CI): m/e =363 (MH+).

IR (KBr) $\nu_{max}$:1715 ($CO_2$ H) cm$^{-1}$.

$1_H$ NMR ($CDCl_3$) δ: 1.21 (6 H, m, $CH_2$), 1.55 (2 H, quintet, J =7 Hz, $CH_2$), 1.74 (2 H, quintet, J =7 Hz, $CH_2$), 2.29 (2 H, t, J =7 Hz, $CH_2 \cdot CO_2$ H), 3.99 (2 H, t, J =7 Hz, N—$CH_2$), 7.05 to 7.55 (10 H, m, aryl H), and 7.76 (1 H, s, pyrazole H).

Anal. Calcd. for $C_{23}H_{26}N_2O_2$:
C, 76.21; H, 7.23; N, 7.73;
Found: C, 76.37; H, 7.26; N, 7.80.

What is claimed is:

1. A compound of the formula

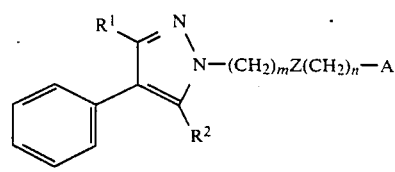

wherein
R$^1$ and R$^2$ each are independently hydrogen or phenyl, provided that R$^1$ and R$^2$ may not both be hydrogen;
m is an integer from 3 to 9;
n is an integer from 0 to 3 and the sum of
m+n is an integer from 5 to 12;
Z is O, S, SO, $SO_2$, —CH=CH— or a direct bond;
A is

R$^3$ is hydrogen or $C_{1-6}$ alkyl;
or a pharmaceutically acceptable salt or hydrate thereof.

2. A compound of claim 1 having the formula

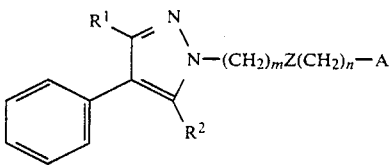

wherein

R¹ and R² each are independently hydrogen or phenyl provided that R¹ and R² may not both be hydrogen;

m is an integer from 3 to 9;

n is an integer from 0 to 3 and the sum of m+n is an integer from 6 to 10;

Z is O, S, —CH=CH— or a direct bond;

A is

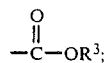

; and

R³ is hydrogen;

or a pharmaceutically acceptable salt or a hydrate thereof.

3. A compound of claim 2 having the formula

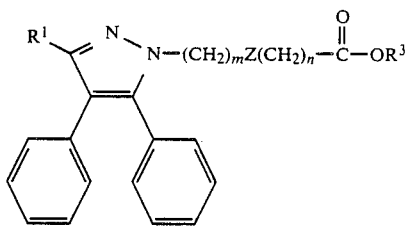

wherein

R¹ is hydrogen or phenyl;

m is an integer from 3 to 9;

n is an integer from 0 to 3 and the sum of m+n is an integer from 6 to 10;

Z is O, S, —CH=CH— or a direct bond; and

R³ is hydrogen;

or a pharmaceutically acceptable salt or a hydrate thereof.

4. The compound of claim 1 which is [[6-(3,4,5-triphenyl-1H-pyrazol-1-yl)hexyl]oxy]acetic acid, or a pharmaceutically acceptable salt or a hydrate thereof.

5. The compound of claim 1 which is 3,4,5-triphenyl-1H-pyrazole-1-octanoic acid, or a pharmaceutically acceptable salt or a hydrate thereof.

6. The compound of claim 1 which is (Z) and (E)-9-(3,4,5-triphenyl-1H-pyrazol-1-yl)-5-nonenoic acid or a pharmaceutically acceptable salt or a hydrate thereof.

7. The compound of claim 1 which is 3,4,5-triphenyl-1H-pyrazole-1-nonanoic acid, or a pharmaceutically acceptable salt or hydrate thereof.

8. The compound of claim 1 which is 3,4-diphenyl-1H-pyrazole-1-nonanoic acid, or a pharmaceutically acceptable salt or hydrate thereof.

9. The compound of claim 1 which is 4,5-diphenyl-1H-pyrazole-1-nonanoic acid, or a pharmaceutically acceptable salt or hydrate thereof.

10. The compound of claim 1 which is [[6-(3,4,5-triphenyl-1H-pyrazol-1-yl)hexyl]thio] acetic acid, or a pharmaceutically acceptable salt or hydrate thereof.

11. The compound of claim 1 which is [[5-(3,4,5-triphenyl-1H-pyrazol-1-yl)pentyl]thio] acetic acid, or a pharmaceutically acceptable salt or hydrate thereof.

12. The compound of claim 1 which is methyl 3,4,5-triphenyl-1H-pyrazole-1-nonanoate.

13. The compound of claim 1 which is 3,4,5-triphenyl-1H-pyrazole-1-decanoic acid, or a pharmaceutically acceptable salt or hydrate thereof.

14. The compound of claim 1 which is [[6-(3,4,5-triphenyl-1H-pyrazol-1-yl)hexyl]sulfinyl]acetic acid, or a pharmaceutically acceptable salt or a hydrate thereof.

15. The compound of claim 1 which is 4,5-diphenyl-1H-pyrazole-1-octanoic acid, or a pharmaceutically acceptable salt or hydrate thereof.

16. A method for inhibiting blood platelet aggregation in a mammal which comprises administering a therapeutically effective amount of a compound of claim 1 or a pharmaceutically acceptable salt or hydrate thereof.

17. The pharmaceutical composition for inhibiting blood platelet aggregation comprising a therapeutically effective amount of a compound of claim 1 or a pharmaceutically acceptable salt or hydrate thereof and a pharmaceutical carrier.

* * * * *